United States Patent [19]

Yamamoto et al.

[11] 4,294,667
[45] Oct. 13, 1981

[54] CORROSION EVALUATION TESTING METHOD OF COATED METALLIC MATERIAL AND APPARATUS EMPLOYED THEREFOR

[75] Inventors: Takashi Yamamoto, Kyoto; Hiroshi Amako, Hirakata, both of Japan

[73] Assignee: Nippon Paint Co., Ltd., Osaka, Japan

[21] Appl. No.: 130,443

[22] Filed: Mar. 14, 1980

[30] Foreign Application Priority Data

May 10, 1979 [JP] Japan .................................. 54-57868

[51] Int. Cl.³ ..................... G01N 27/30; G01N 27/46
[52] U.S. Cl. ................................. 204/1 T; 204/195 C
[58] Field of Search ........................... 204/1 C, 195 C

[56] References Cited

U.S. PATENT DOCUMENTS

| | | | |
|---|---|---|---|
| 3,498,900 | 3/1970 | Banks et al. | 204/195 C |
| 3,649,472 | 3/1972 | Morrissey et al. | 204/1 C |
| 3,766,040 | 10/1973 | Wellborn, Jr. | 204/180 R |
| 4,019,129 | 4/1977 | Grau | 324/30 R |

FOREIGN PATENT DOCUMENTS

| | | | |
|---|---|---|---|
| 2041121 | 3/1971 | Fed. Rep. of Germany | 204/1 C |
| 2252486 | 5/1973 | Fed. Rep. of Germany | 204/1 C |

Primary Examiner—Aaron Weisstuch
Attorney, Agent, or Firm—Wenderoth, Lind & Ponack

[57] ABSTRACT

A method for obtaining electrochemical information significant for corrosion evaluations of a coated metallic material and an apparatus for automatically performing the method.

The electrochemical information is detected and stereoscopically displayed to show respective features of any kind of corrosions. The above-described apparatus is arranged to constitute a system which can automatically electrochemically measure the corrosion preventing performance of the coated film in any kind of corrosive medium.

28 Claims, 53 Drawing Figures

Fig. 1 Block Diagram
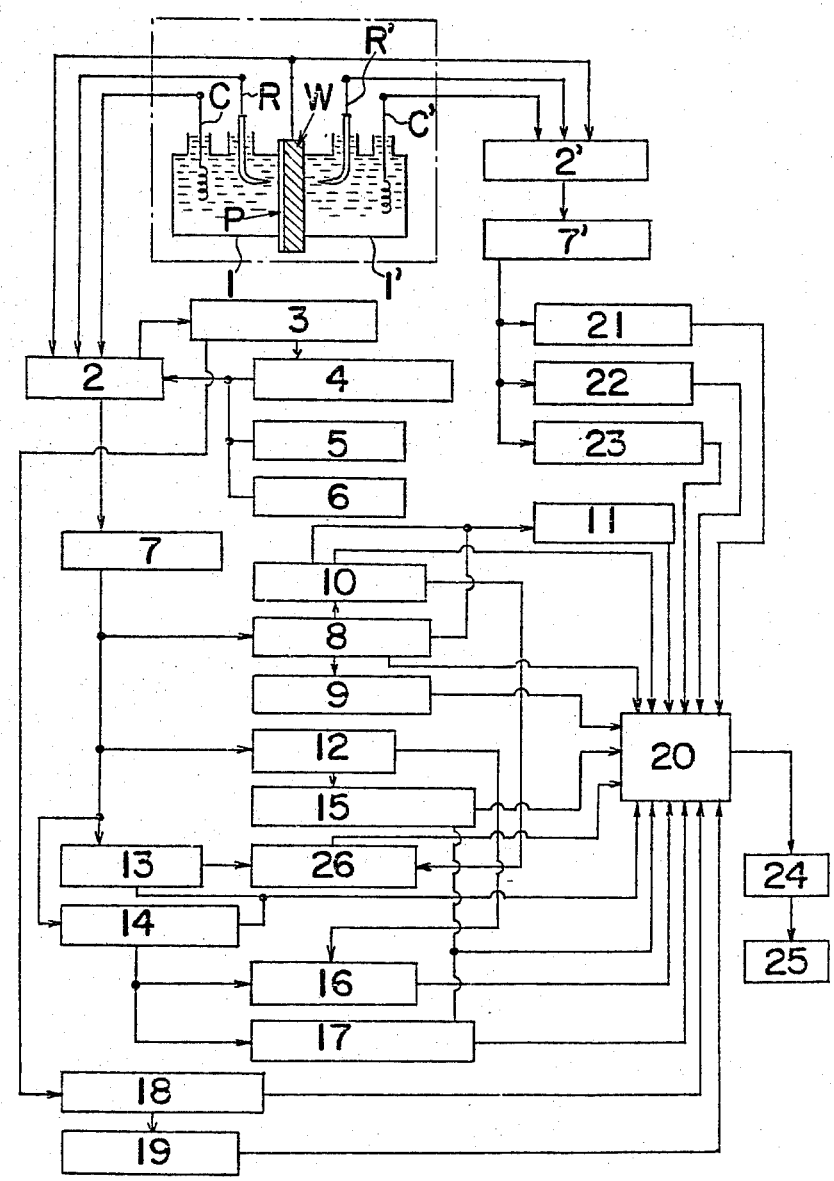

Fig. 2 Schematic Cross-Section of Cells
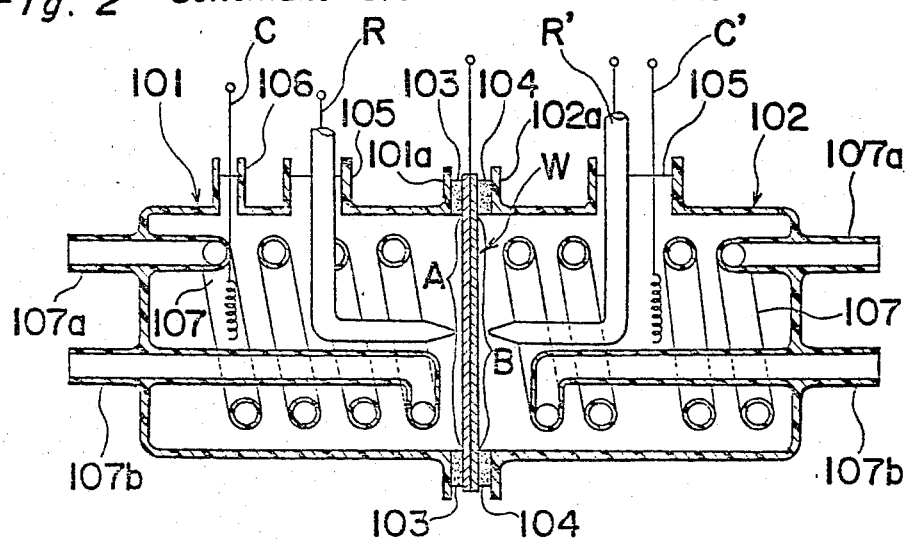
Fig. 3
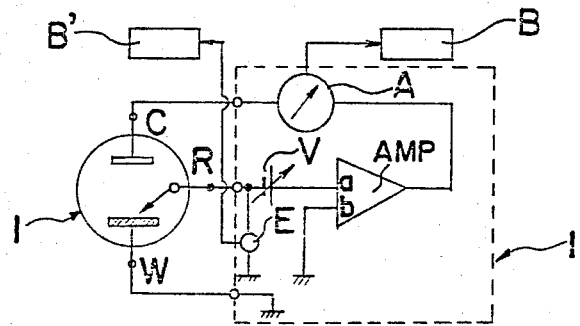
Fig. 4 Block Diagram of 3
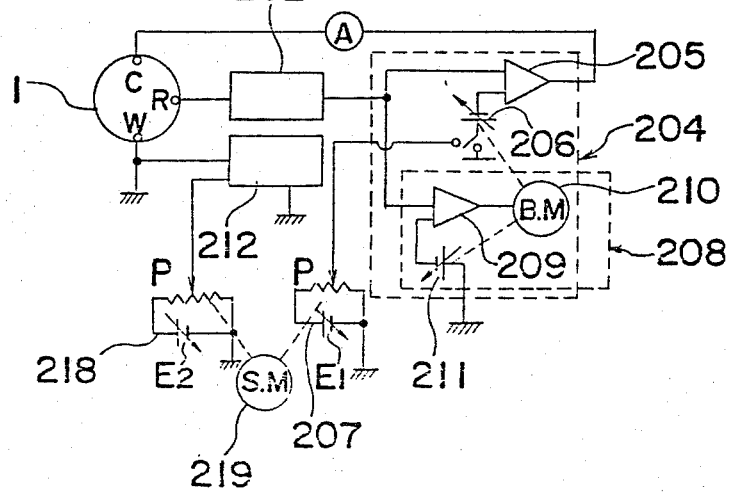

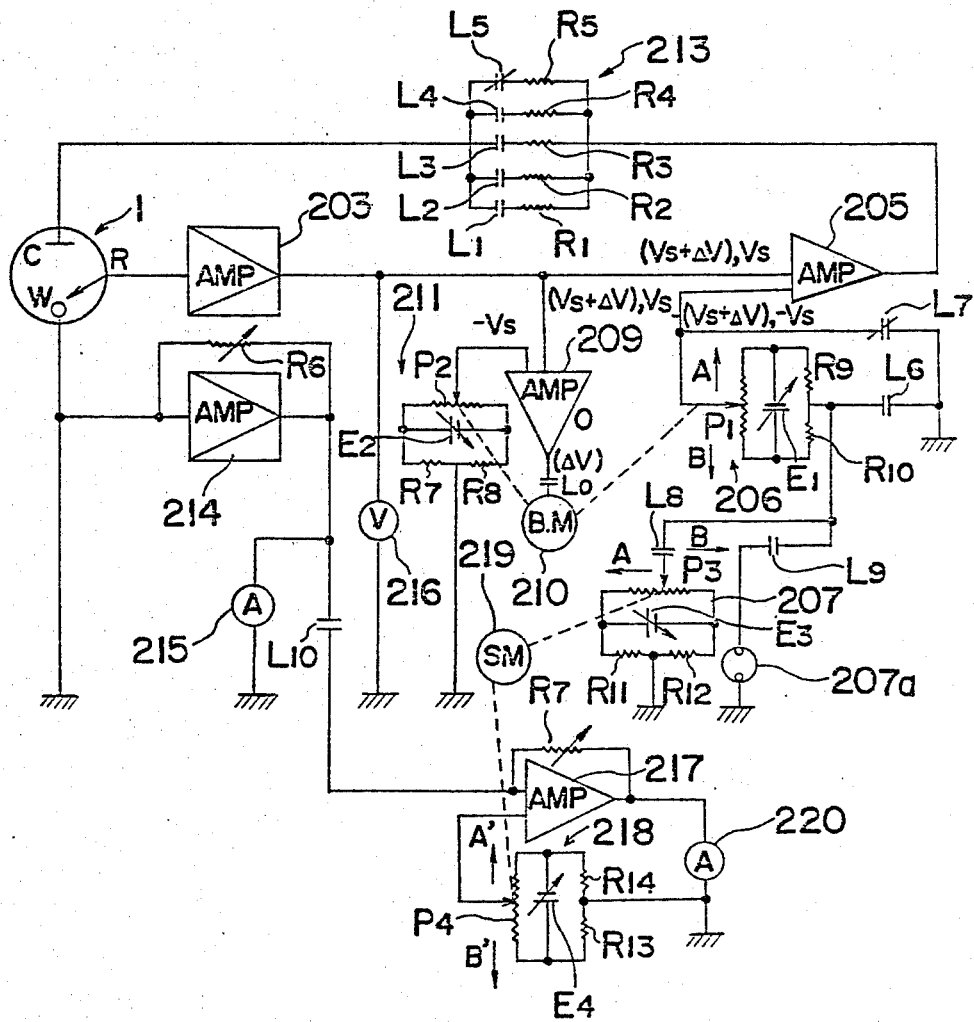
Fig. 5  Circuit of 4

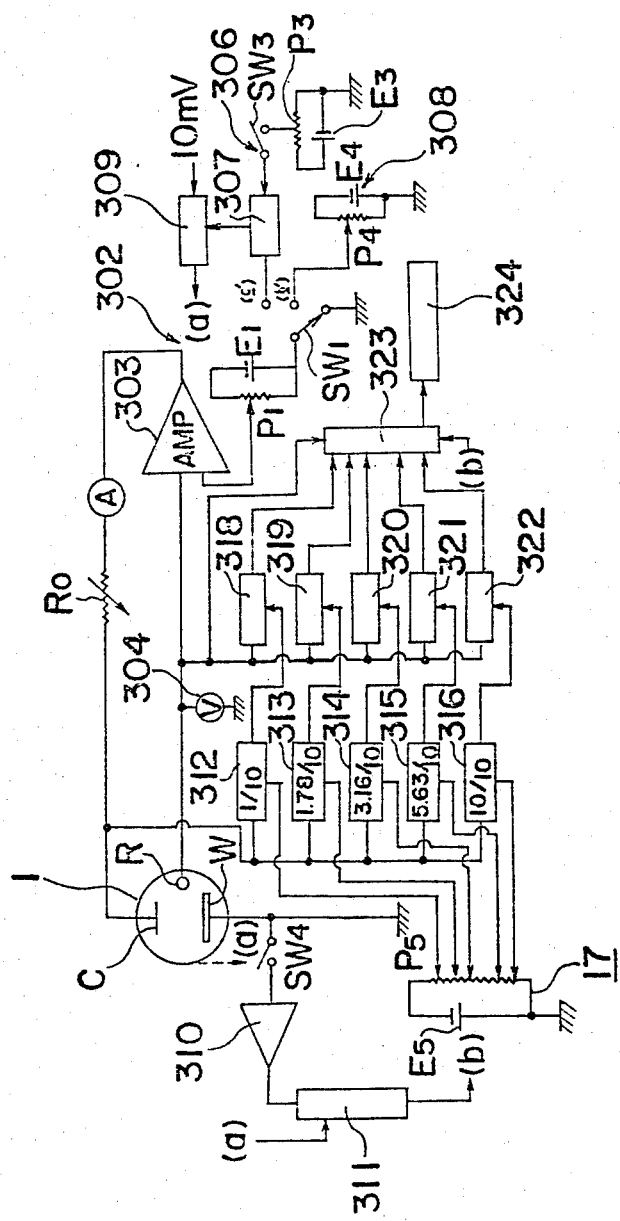
Fig. 6 Detector Circuit

Fig. 7 Graph: Corrosion Current v Corrosion Potential
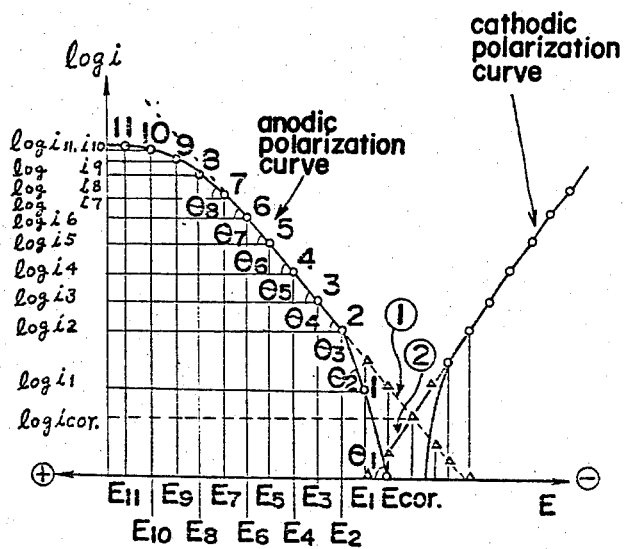
Fig. 8 Diagram of Electrolyzer
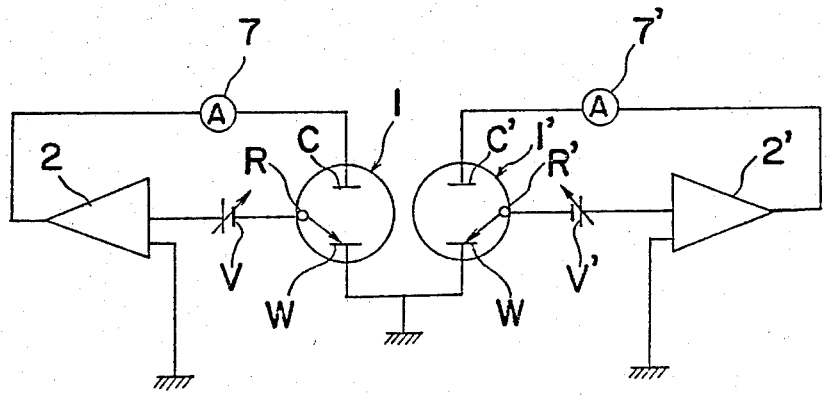

Fig. 9 Automatic Electrolyzer Circuit
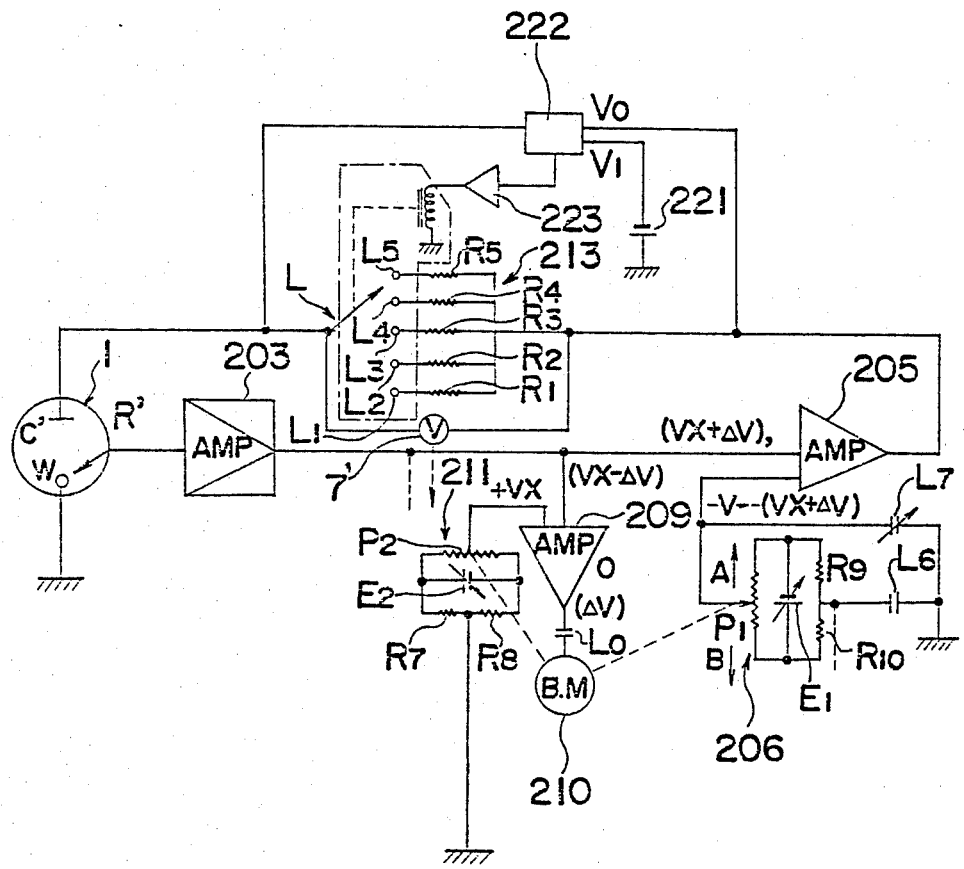
Fig. 10
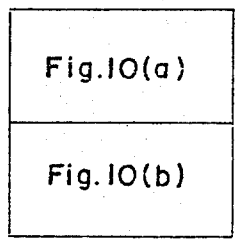
Fig. 11
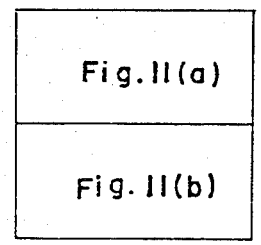

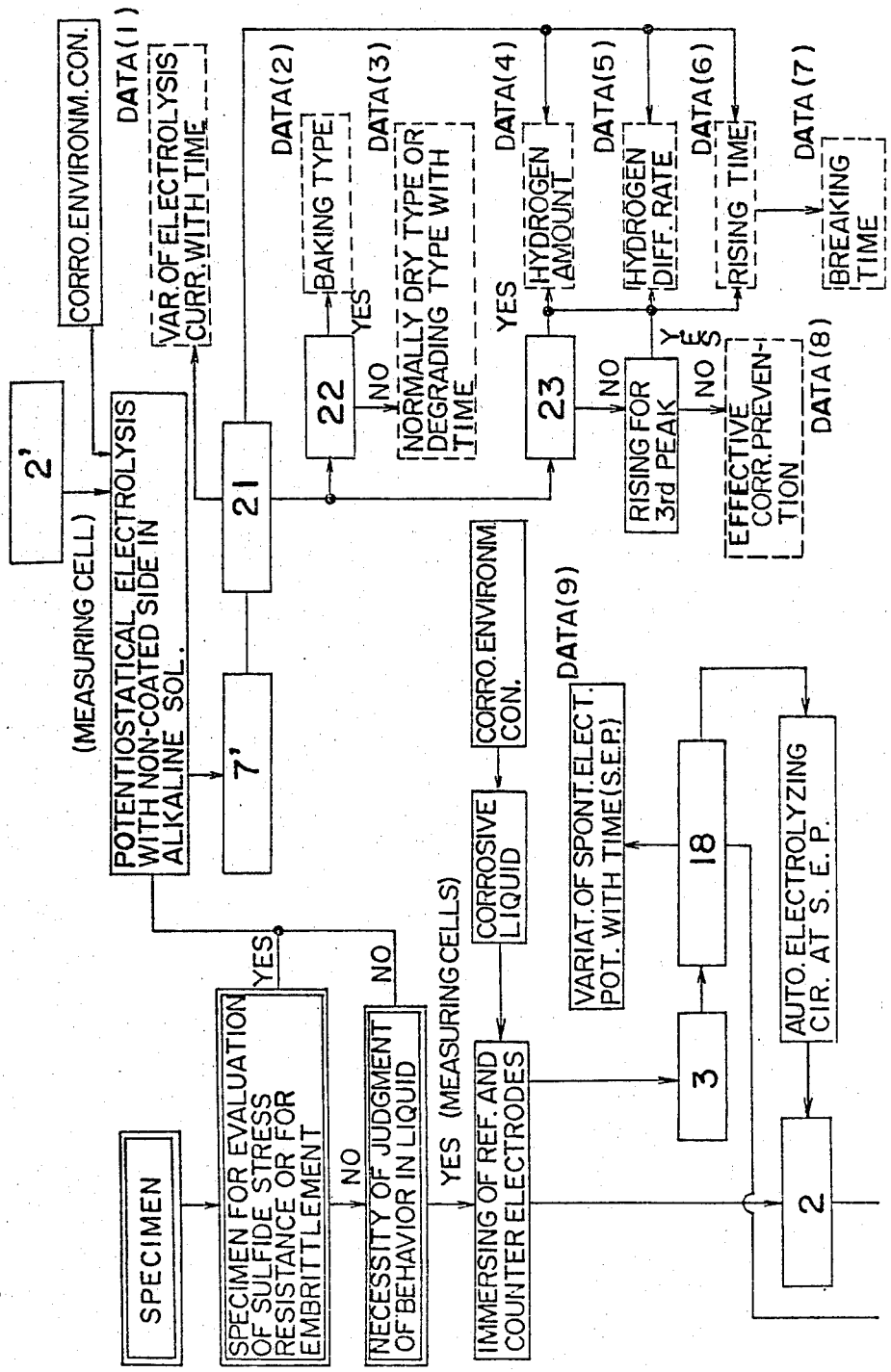
Fig. 10(a) Corrosion Test Flow Chart

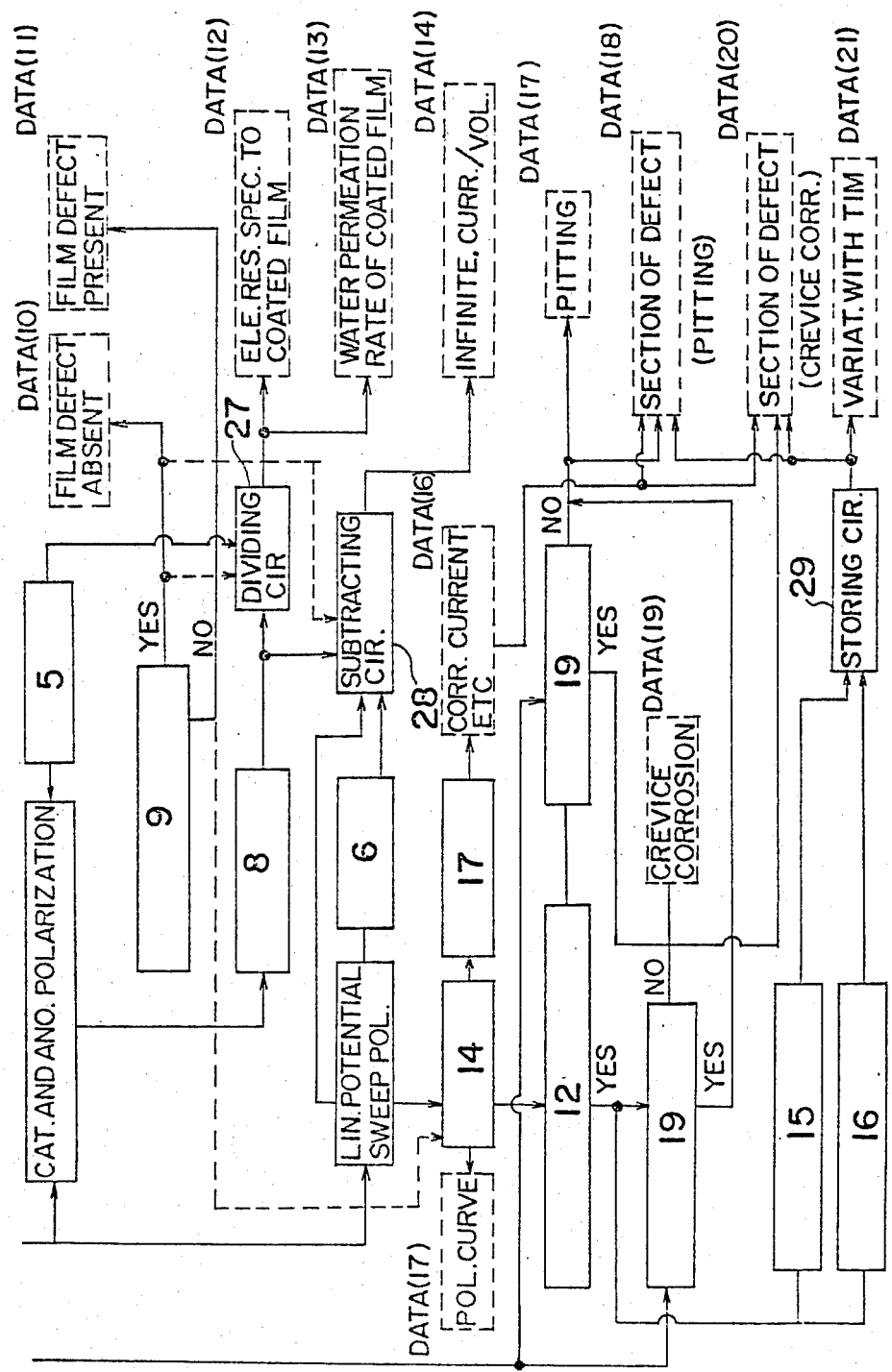
Fig. 10 (b) Corrosion Test Flow Chart (Cont.)

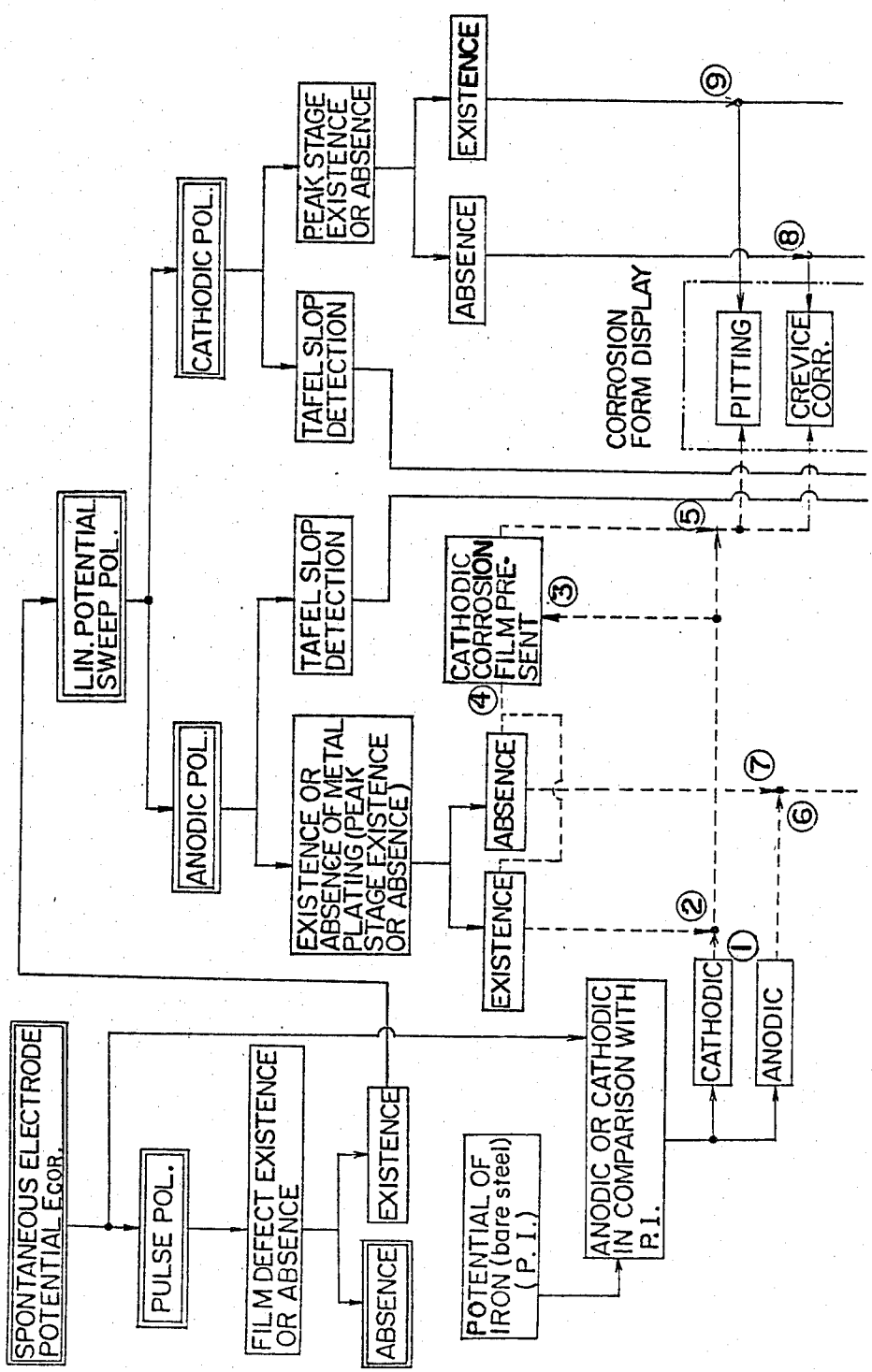
Fig. 11(a) Flow Chart: Model Diagram

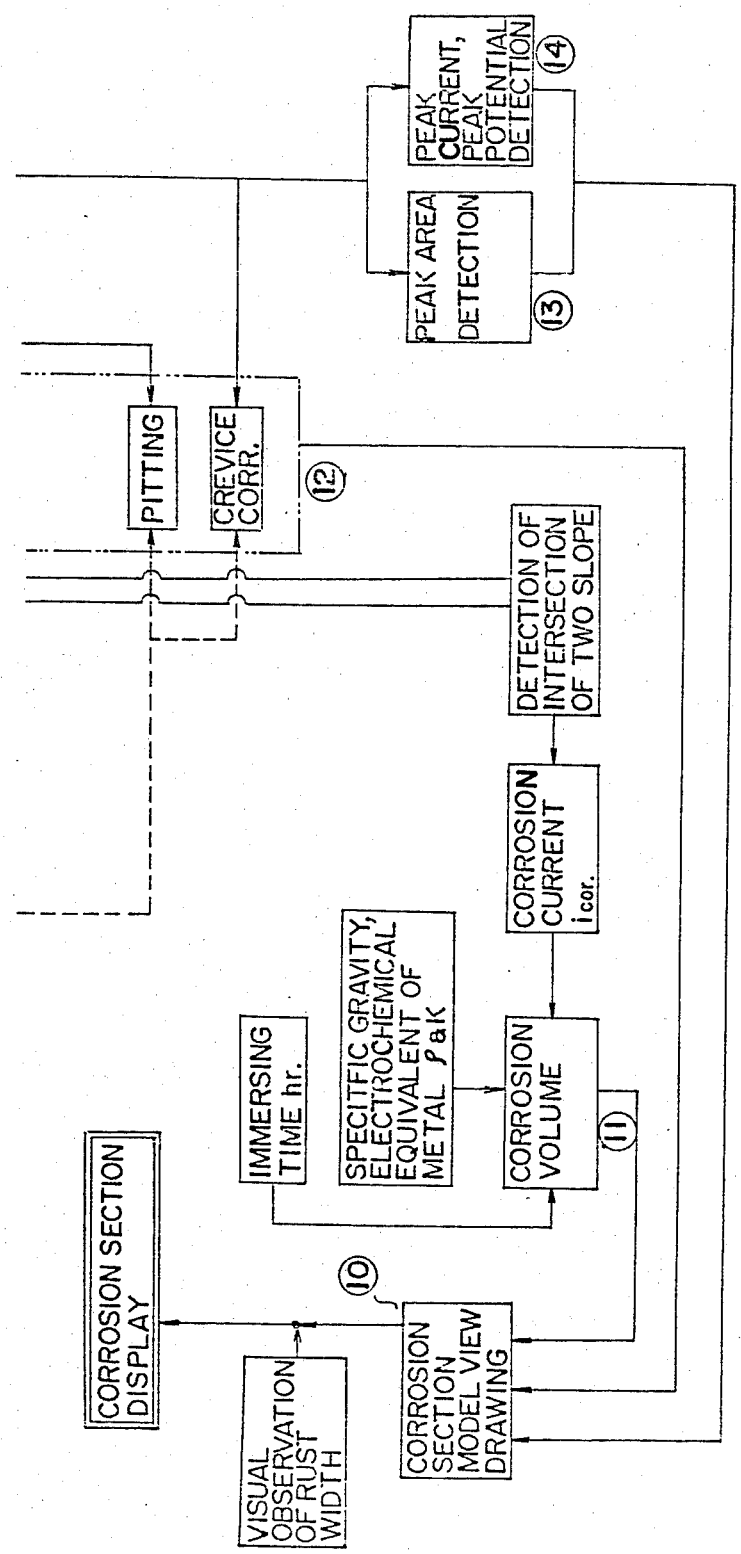
Fig. 11(b) Flow Chart: Model Diagram

Fig. 12 Voltage Pulse Train
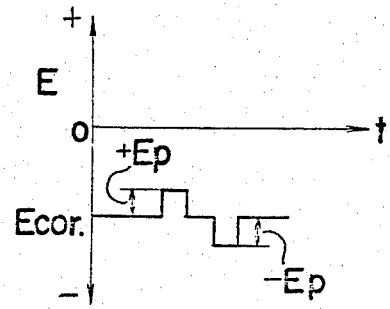
Fig. 13 Current Pulse Train
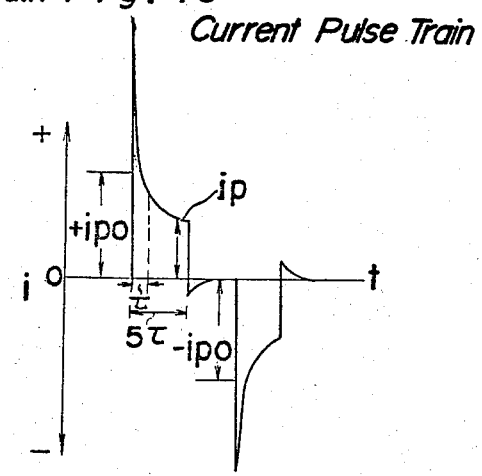
Fig. 14 Voltage vs Time
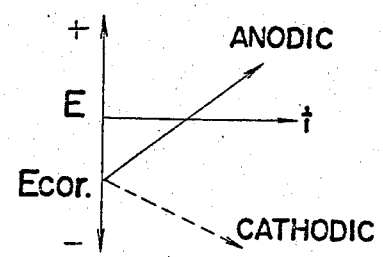
Fig. 15 Current vs Time
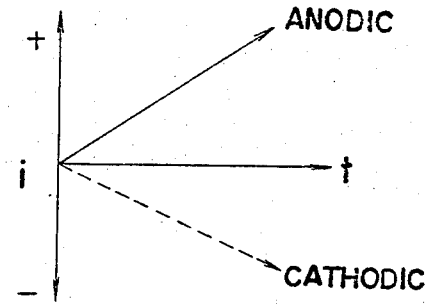
Fig. 16 Small current-voltage
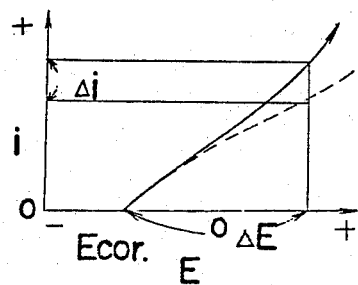

Fig. 17
Cathode Polarization
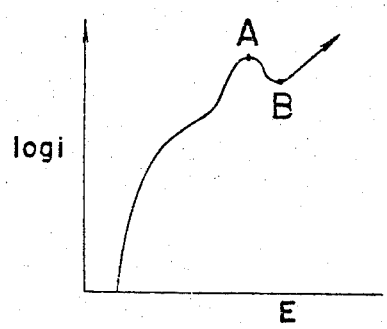
Fig. 18
Peak Cathode Polarization
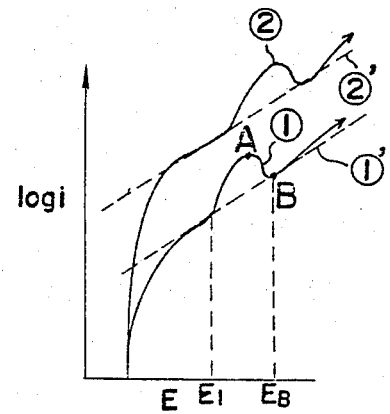
Fig. 19
Peak Cathode Polarization
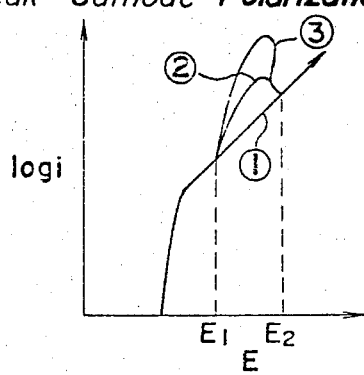
Fig. 20 "Pitting"
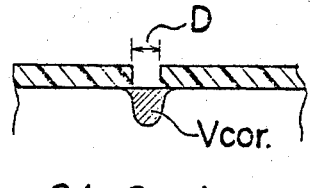
Fig. 21 Crevice
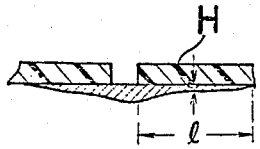
Fig. 22
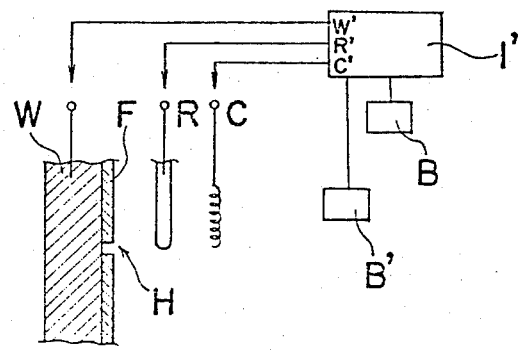

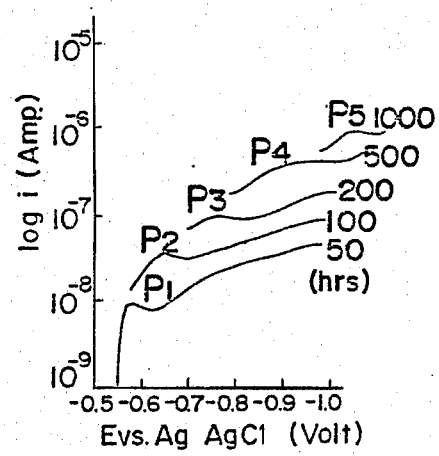
Fig. 23 Cathode Polarization (Embod. 1)
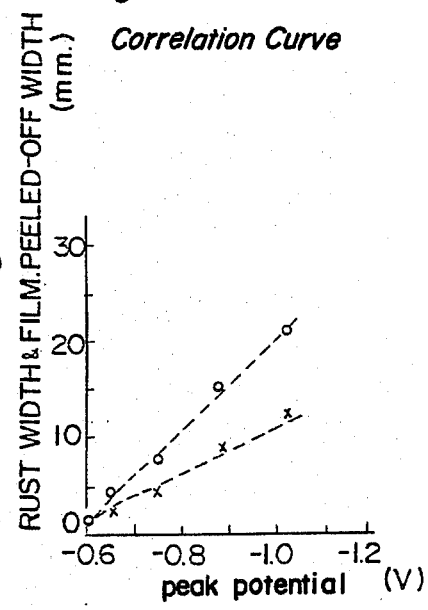
Fig. 25 Correlation Curve
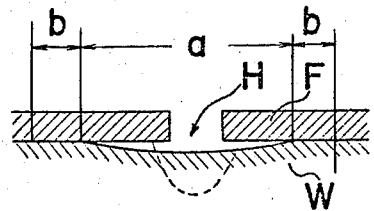
Fig. 24 Corrosion Form
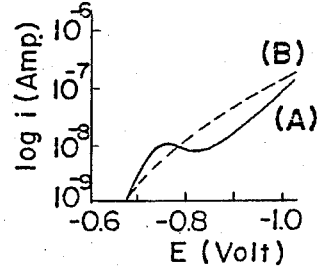
Fig. 26 Cath. Polarization (Embodiment 2)
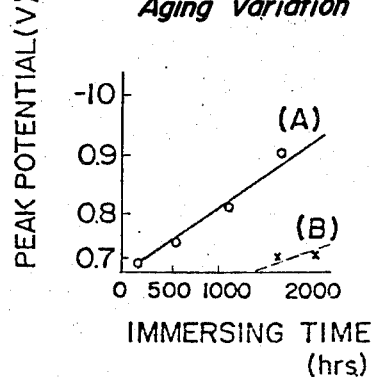
Fig. 27 Embod. 1 Aging Variation
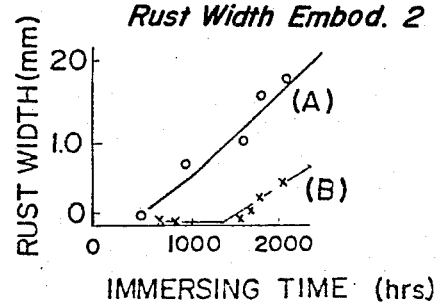
Fig. 28 Rust Width Embod. 2

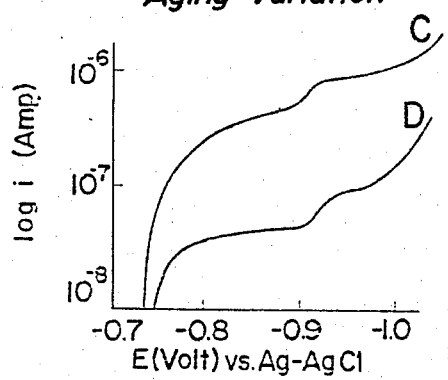
Fig. 29 Embod. 3 Aging Variation
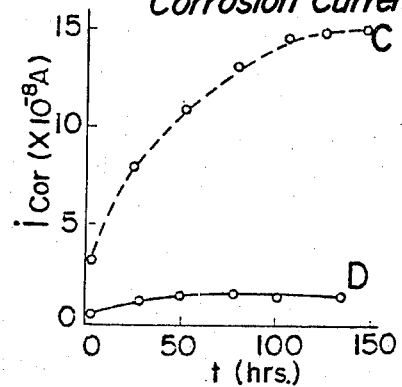
Fig. 30 Embod. 3 Corrosion Current
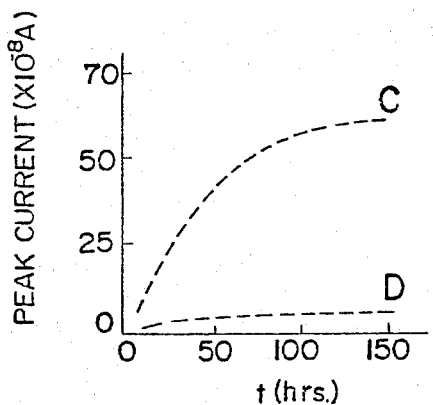
Fig. 31 Embod. 3 Peak Current
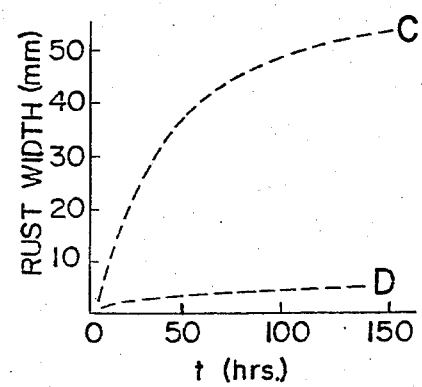
Fig. 32 Embod. 3 Rust Width
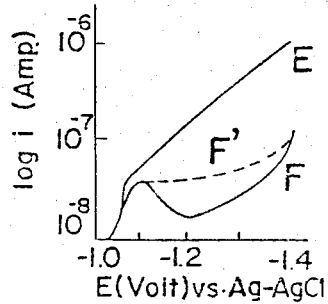
Fig. 33 Embod. 4 Cath. Pol. Curve
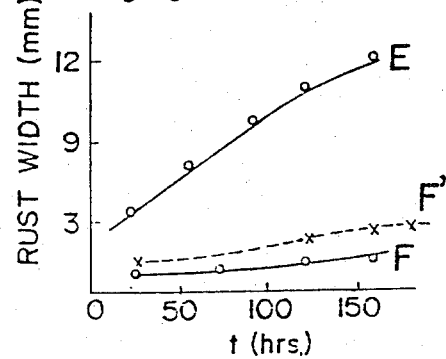
Fig. 34 Embod. 4 Aging Variation

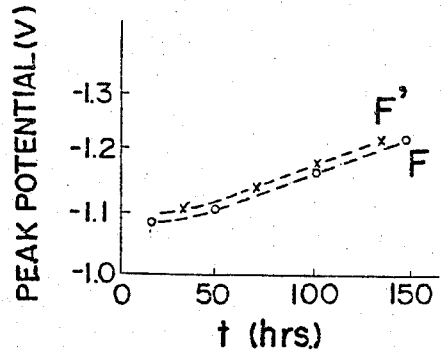
Fig. 35 Aging Variation
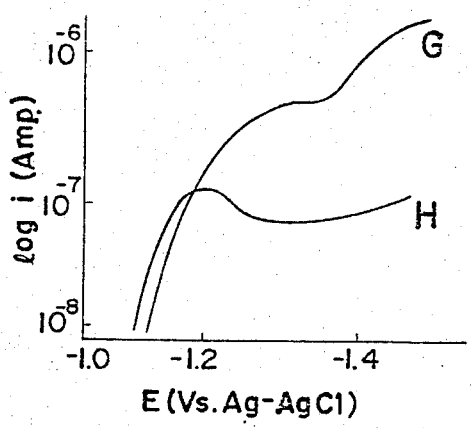
Fig. 36 (a) Cathodic Polarization
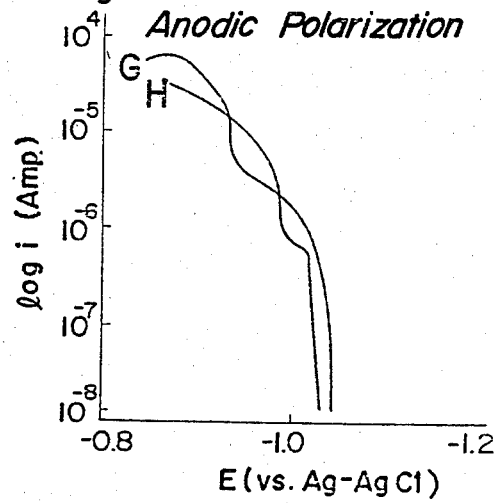
Fig. 36 (b) Anodic Polarization
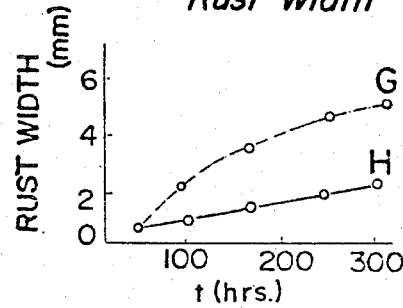
Fig. 37 Embod. 5 Rust Width
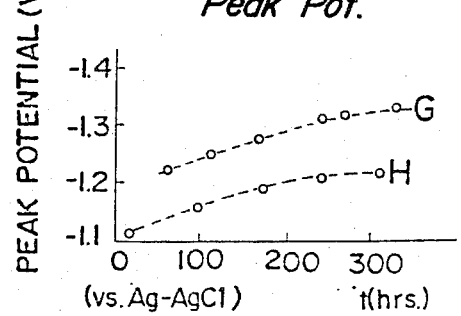
Fig. 38 Embod. 5 Peak Pot.

Fig. 39 Embod. 6 Cathode Pol. Specimen H
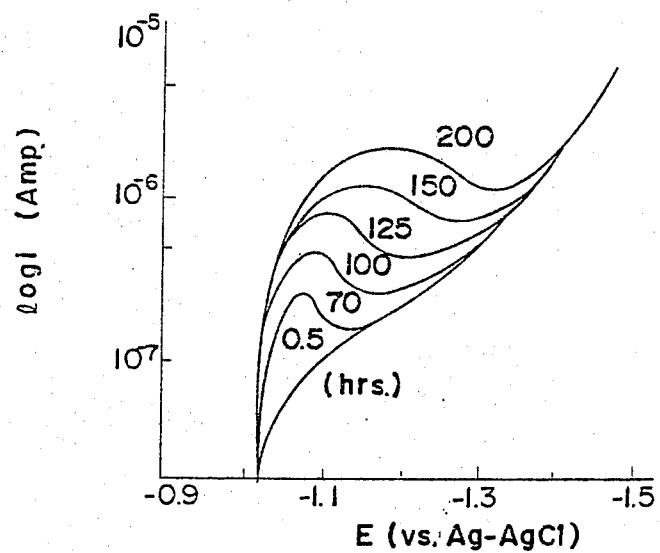
Fig. 40 Embod. 6 Cathode Pol. Specimen I
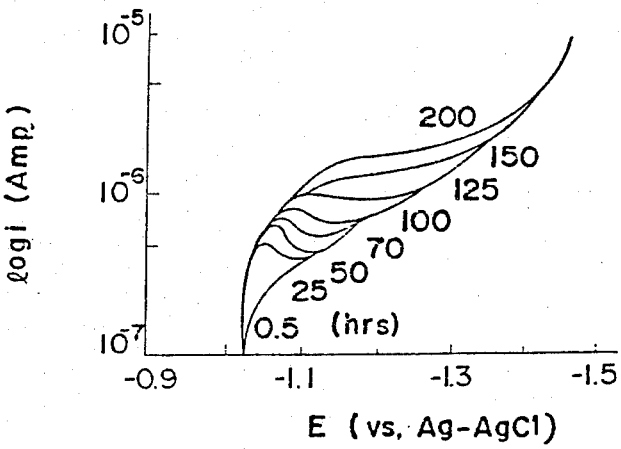

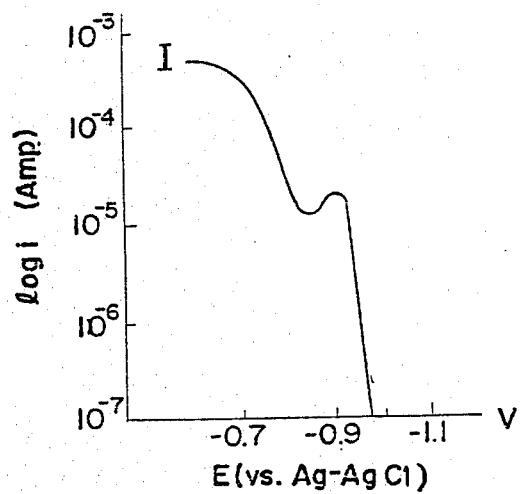
Fig. 41 Embod. 6
Anodic Polarization
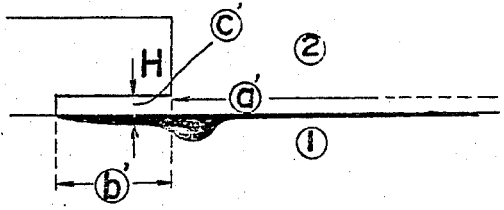
Fig. 42 Clearance Corrosion
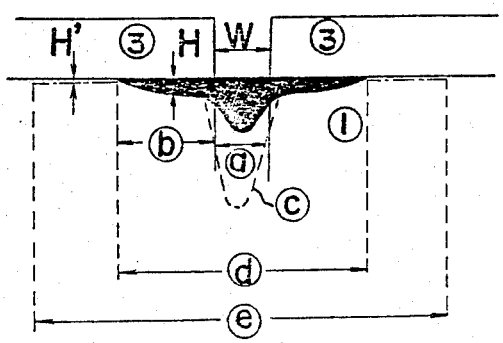
Fig. 43 Corrosion Illustrated

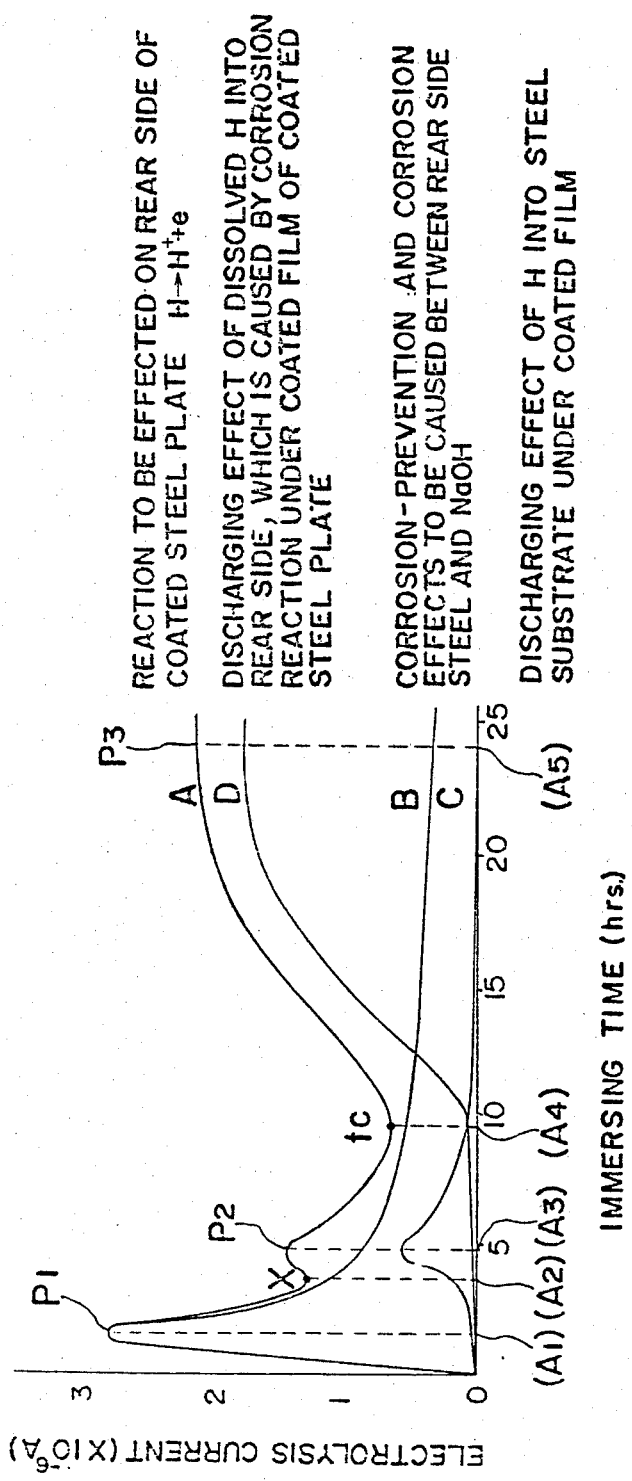
Fig. 44 Aging Variation-Electrolysis Current

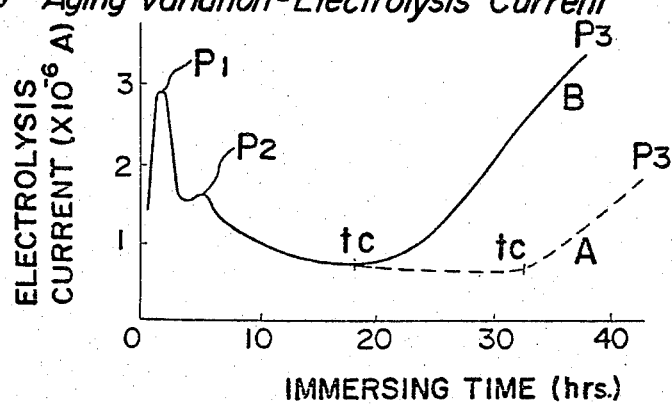
Fig. 45  Aging Variation-Electrolysis Current
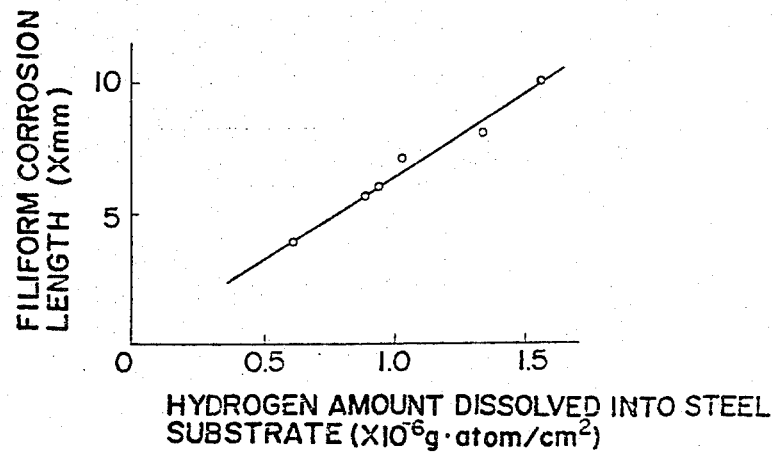
Fig. 46  Filiform
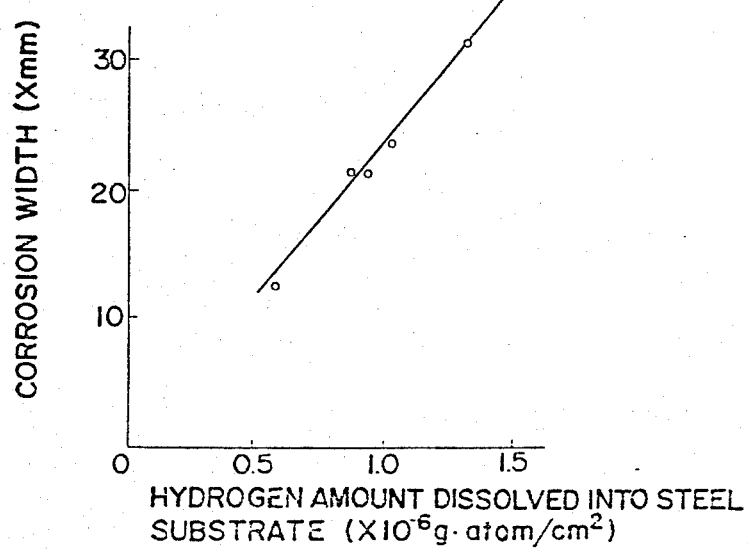
Fig. 47  Filiform Fig. 48 Filiform
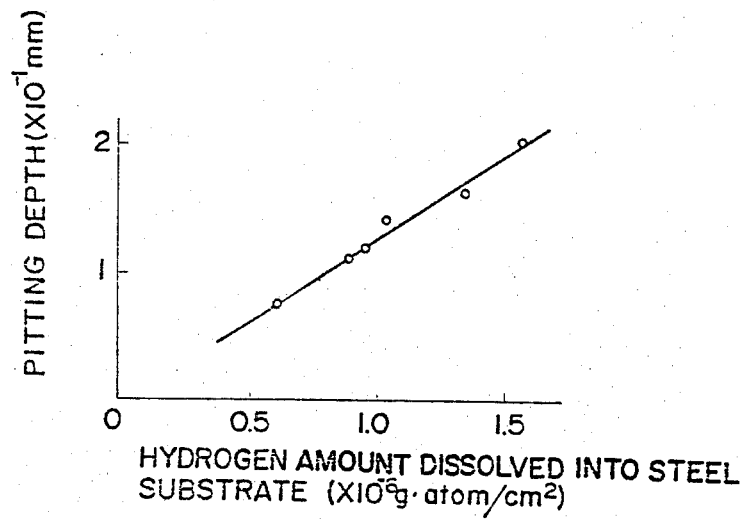
Fig. 49 Aging Variation-Current
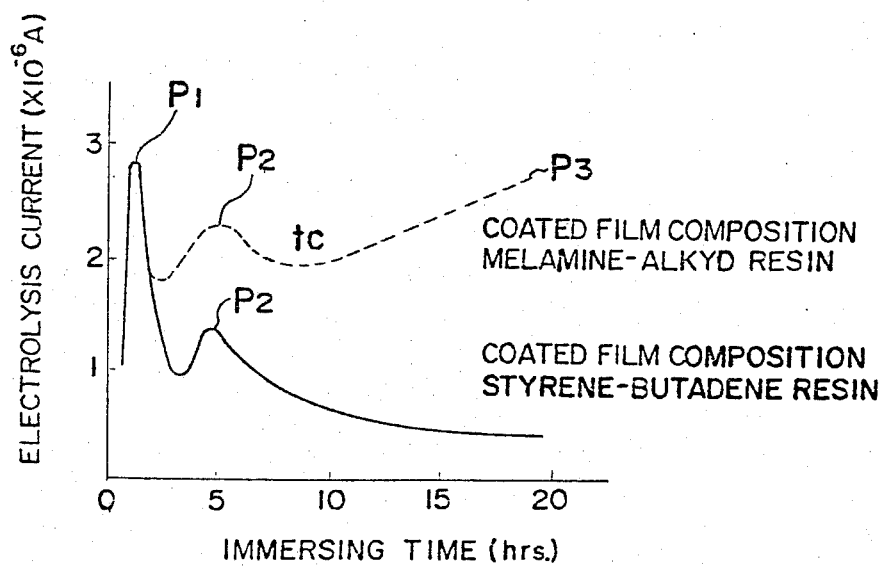

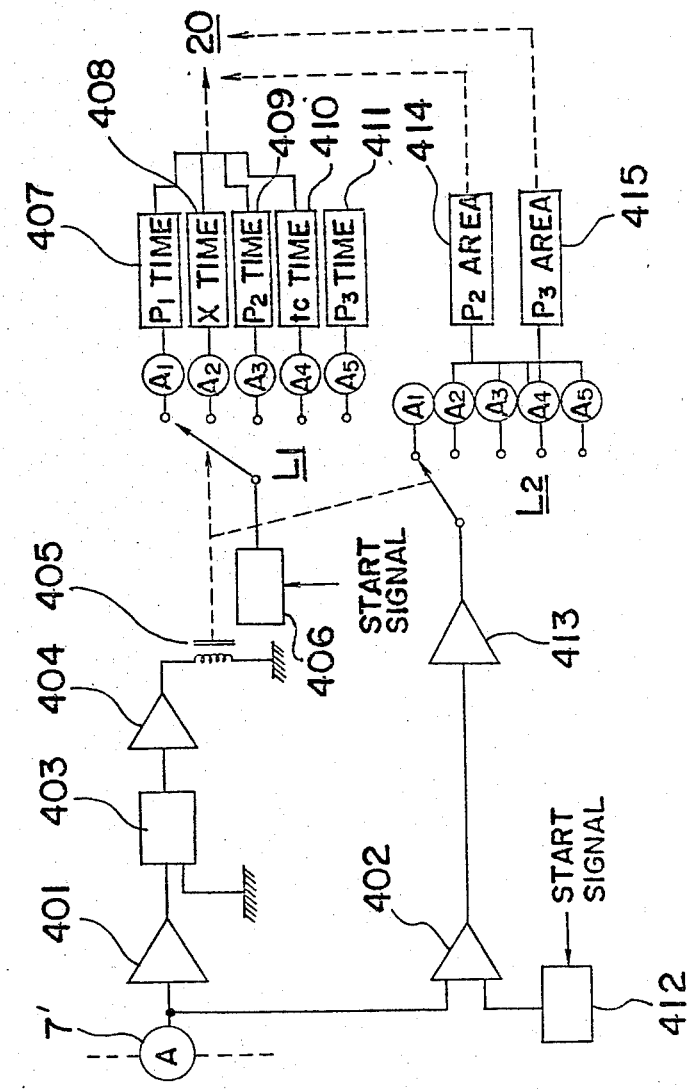
Fig. 50 Peak Detector

CORROSION EVALUATION TESTING METHOD OF COATED METALLIC MATERIAL AND APPARATUS EMPLOYED THEREFOR

BACKGROUND OF THE INVENTION

This invention relates to a test for evaluating corrosion and more particularly, to a corrosion evaluation testing method and apparatus for coated metallic material.

Generally, metallic material is coated on its surface with a film for preventing corrosion. The corrosion preventing performance of such coated film strongly depends on the resistance-polarization caused by the electric resistance of the coated film. Accordingly, various films of high resistance have been adapted to be coated on, for example, steel plate, etc. However, water still cannot be completely shut out even after application of a coating film of the above described type onto metallic material. Accordingly, corrosion progresses underneath the film. Also, when defects exist in the coated film, the corrosion in the defective portion of the film progresses more rapidly as the electric resistance of the film becomes higher. Thus, so-called "chipping corrosion" caused by film damage and cracks presents a serious problem.

In addition to the resistance-polarization described above, physicochemical effects can be caused under environmental conditions by a corrosive liquid; for example, preventing or promoting effects inherently caused by substances melted and discharged from the film, including pigments, must be taken into account.

At present, method of coated steel plate is tested for corrosion by a spontaneous or weathering exposure test, a dipping or immersing test, artificially accelerated exposure tests or the like. However, in the conventional methods, the specimens to be tested are first subjected to controlled damage and thereafter the corrosion results are simply observed visually; thus, the phenomenological mechanism relating the coated steel plate and to the testing method has not yet been sufficiently clarifed. Therefore, significant information for developing an improved film coating cannot be expected to be obtained with the conventional methods.

In addition, in response to an anodic corrosion of the coated steel plate, a cathodic reaction is in general caused in the neighborhood of the area wherein the above described anodic reaction is taking place. Thus, the corrosion phenomenon of hydrogen fragility corrosion or hydrogen cracking, etc. caused by the diffusion of atomic hydrogen, which is produced by the cathodic reaction, into the steel should not be overlooked from the view point of preventing the structure from being cracked by the corrosion phenomena. Furthermore, it is important to know the corrosion preventing capability of the film in corrosive liquids other than the electrolytes (for example, crude oil) and in soils or corrosive gases.

In order to quantitatively analyze the corrosion phenomenon relating to coated steel plate, first the phenomenological information of physicochemical quantities concerning the corrosion must be obtained. An electrochemical method by which the process of corrosion reaction can be easily traced is particularly suitable for this type of corrosion evaluation. However, since the film coated on the steel plate is high in resistance, a reliable measuring result necessary for estimating the corrosion reaction mechanism, cannot be obtained by the same electrochemical method used for measuring bare steel.

After much research the present inventors have developed a method based upon the potentiostatic electrolysis of the coated steel plate at the spontaneous electrode potential. The method includes a method of obtaining the polarization curve, a method of detecting the extremely small amount of current-potential variation or an infinitesimally small current-potential variation, and a method of detecting the film resistance specific to the coated film. Moreover, a method has been developed for detecting the electrolysis current of the discharge of the atomic hydrogen which is diffused into the non-film side from the film side; in the method the non-film coated side of the coated plate is potentiostatically electrolyzed at the spontaneous electrode potential. Thus, a basic object of the present invention is to establish a corrosion evaluation testing method for coated metallic material and associated apparatus. This comprises a method for detecting electrochemical information significant to the corrosion evaluation by subjecting coated metallic material to a series of electrochemical testing methods developed according to the present invention; there is also an apparatus for automatically performing the detecting method according to the type of specimen and evaluation needed.

Furthermore, up to the present, to evaluate corrosion at defects in a film coating conventionally a method of first providing cross-cuts on the film face of a coated specimen and then, visually observing the blistering and rust width near the cuts has been employed. However, with the conventional method, it is difficult to judge or confirm, from the outside, the corrosion forms, i.e., whether the corrosion tends to spread out under the film along the film defect portions ("crevice") or in depth below the original defect portions ("pitting"). Moreover, it is not practical to apply such corrosion prior art evaluating tests when the coated metallic objects are buried in water or in the soils. On the other hand, various electrochemical methods of measuring the electrode potential, etc. of the coated metallic object have also been conventionally performed. However, these prior methods are still insufficient for use in the corrosion evaluating test, because these electrochemical methods inherently involve complicated analyses.

Regarding the kinds of defects usually introduced in the conventional methods, the present inventors have found, after the various experiments on the polarization behavior of the coated metallic face by the use of the newly developed present method, that the peak portion will appear in the polarization curve when a coated metallic material whose film coat has defects is polarized in a cathodic mode. Also, the inventors' analysis, shows that a certain relationship can exist between the existence of a peak portion and the form of corrosion (corrosion form) in the film defect portion. Thus, the another object of the present invention is to provide an electrochemical method and an apparatus for detecting the corrosion form or structure in the film defect portion of the coated metallic plate material, so that this information can be used in the corrosion evaluation.

As described earlier, if the corrosion preventing performance of the film is properly quantitatively treated, it is not necessary to directly electrochemically measure the corrosion preventing performance of the film in the corrosive gases (such as steams), soils or non-electrolytes (such as crude oil).

SUMMARY OF THE INVENTION

Accordingly, an essential object of the present invention is to provide a corrosion evaluation testing method for coated metallic material and an apparatus employed therefor. These are for detecting the electrochemical information useful for corrosion evaluation of the coated metallic material by applying upon the coated metallic material a planned series of electrochemical testing steps developed according to the present invention. Further the invention includes an apparatus for automatically performing the detecting method disclosed.

Another important object of the present invention is to provide a corrosion evaluation testing method for coated metallic material and associated apparatus of the above-described type, comprising an electrochemical method and an apparatus for detecting the corrosion form (e.g., "crevice" or "pitting") in the film defect portion of the coated metallic material.

A further object of the present invention is to provide a corrosion evaluation testing method for film coated metallic material and an apparatus therefor to electrochemically determine the expected corrosion preventing performance of the film even with respect to corrosive gases, steams, soils and crude oils.

A still further object of the present invention is to provide a corrosion evaluation testing method for coated metallic material and an apparatus therefor overcoming the disadvantages of the prior art.

With respect to corrosion testing one method according to the present invention comprises the steps of:

applying, upon at least one face of a specimen metallic plate, paint whose film performance is to be examined, and then exposing it to the given corrosion medium;

potentiostatically electrolyzing the film side of the specimen plate at its spontaneous electrode potential with respect to the corrosive medium; polarizing the film side face of the specimen plate by pulse-polarization, etc. to detect if the film face has defects;

when the film is found not to have defects, detecting an infinitesimally small current-potential variation, by compensating for polarization current due to the electrical resistance of the coated film.

But when the coated film is found to have defects, the method calls for next detecting anodic and/or cathodic polarization curves.

When the behavior judgement of the film in the above-described corrosion medium can not be made or is not needed for example, when the medium is a solid, gas or non-electrolyte liquid, a non-film face on the reverse face of the film face of the specimen plate is brought in contact with an alkaline solution so that the electrolysis current effected by ionization in the non-film face may be detected.

For the sake of concisely summarizing the present invention, in order to distinguish between the electrolysis current to be effected on the film-face side and the electrolysis current to be effected on the non-film-face side, the film face electrolysis current is designated "polarization current", and the non-film face electrolysis current is designated "electrolysis current".

In the above method, when the pulse polarization method is adopted to determine if there is a film defect, the pulse current flowing between the film face of the coated metallic plate and a counter electrode is used to measure the electric resistance of the film, this permits determination of the water absorption or permeation rate of the film from the measured film resistance. Either pulse polarization or linear potential sweep polarization can be used to detect whether or not the film has defects.

When the film is found not to have defects, the induced polarization curve is rate-determined or governed by the electric resistance specific to the film and becomes almost straight-line. The value of corrosion current can be obtained by computing the resultantly extremely small amount of current-potential variation, after correcting for the polarization current due to the electric resistance specific to the film by subtracting the resistance related current.

When the film is found to have defects, the value of corrosion current can be obtained from cathodic and/or anodic polarization curves.

Particularly, a peak portion may appear in cathodic polarization curve. The present inventors have already found out that the variation in the value of peak potential with respect to the immersing time in the corrosive medium correlates with the variation in the rust width of the film defect portion. Also the aging variation in the value of the current at the peak portion can be correlated with the aging variation of the corrosion current. Accordingly, successive detections of the potential and current at the peak ("peak potential", "peak current") or their aging variations make it possible to obtain the electrochemical information about the aging variation of the rust width and corrosion current, i.e., the corrosion amount as a function of the immersing time of the coated metallic material.

Also, according to the present invention, it has been further confirmed that in the cathodic polarization curve the area relating to the peak or the plateau portion correlates with the rust width. Accordingly, the area or its aging variation can be traced to further clarify the corrosion behavior of the coated metallic material. The variational features of the cathodic polarization curves with respect to the immersing time can be roughly classified into two types. Therefore, the areas relating to the peak portion can be obtained by respective methods correspondingly suitable for these two types.

With respect to an apparatus for performing the method described above, an apparatus according to the present invention can comprise:

a pair of measuring cells for exposing selected regions of a specimen film coated (on one side) plate on opposite sides to a corrosive medium and an alkaline solution;

a first potentiostat means for potentiostatically electrolyzing the film side of the specimen plate in the corrosive medium at the spontaneous electrode potential;

a means for detecting the existence of film defects, as by pulse polarization, etc.;

a second potentiostat means for potentiostatically electrolyzing the non-film side of the specimen plate in the alkaline solution at relative zero potential level with reference to the potential of a non-film side reference electrode;

a control means for controlling the over-all operation of the apparatus; and a means for collecting, recording and calculating the input signals coming from the various detecting means to display on a displaying means outputs necessary for the corrosion evaluation.

Particularly, when the means for detecting the existence of film defects comprises a pulse potential applying means and a pulse polarization current detecting means, the signals from the two means can be used to output a computed electric resistance signal for the film and a computed water permeation signal for the film, the computation taking place with the help of the means for collecting, recording and calculating (a processor means).

When the value of corrosion current is obtained from either the polarization curve or the extremely small amount of current-potential variation as described above, the output of the polarization current detecting means or the extremely small amount of current detecting means and the output of the linear potential applying means are input to the processor means which calculates the corrosion current.

In addition, when a peak portion exists is the cathodic polarization curve the peak potential and peak current are obtained using a peak detecting means connected to both to the polarization current detecting means and to the control means. By the above arrangement, upon receipt of a signal that a peak exists (a peak-existing signal), the peak detecting means actuates a specially provided peak potential and/or peak current detecting means and inputs the detected peak potential and/or peak current signal into the processor means. On the other hand, when the area of the peak (peak area) is required to be determined, the peak area of the cathodic polarization curve is calculated by the processor means in response to the peak-existing signal.

In addition to a peak detecting means capable of differentiating the electrolysis current variation etc., a peak area detecting means capable of integrating the electrolysis current variation and a time-counting means or timer capable of measuring the time elapsed since the measuring start are further provided in the apparatus. Thus, the peak signal from the peak detecting means actuates the timer, by means of the control means, to store and display the time duration of the given peak signal. Furthermore, the signal described above also actuates the peak area detecting means, so that the electrolysis current variation between the given peak signals is first integrated and then, the integrated value is stored and displayed so as to provide the desired measured value of the electrolysis current values from the electrolysis current variation.

With respect to an electrochemical method and an apparatus for detecting the corrosion form in the film defect portion of the coated metallic material, the existence of a peak portion in the cathodic polarization curve of the coated metallic material having the defective film is first confirmed. Then, the coated plate's related spontaneous electrode potential is compared with the known spontaneous electrode potential of the substrate metal, thereby confirming whether the coated plate is cathodic or anodic in comparison with that of the substrate metal. Since the judgement of the corrosion form as described above is qualitative, the result described above and information related to the corrosion current, for example the corrosion volume, is combined according to the present invention to provide a stereoscopic display of the features of the corrosion portion.

Furthermore, the relationship between the existence of the peak or the plateau portion and the corrosion form in the film defect portion region may become reversed, if there is a metal-plated layer or a corrosion prevention film around the cathode between the film and the substrate metallic surface. However, the existence of the metal-plated layer and the existence of the corrosion prevention film around the cathode can be in turn determined by the above-described comparison and/or the detection of the existence of the peak portion in the anodic polarization curve.

In addition, in order to further obtain information related to the rust width of the film defect portion (in the case of crevice corrosion) and the pitting depth (in the case of pitting corrosion), the potential and the current area of the peak are required to be detected when the peak exists in the cathodic polarization curve. The quantity of electricity relating to a second peak and its subsequent portion of the aging variation of the hydrogen ionized current or the quantity of electricity relating to the third peak out of the aging variation of the hydrogen ionized current around the non-film face are arranged to obtain without depending upon the existence of the peaks for the purpose described above. As for an apparatus for embodying the method, a peak detecting means employed for the cathodic polarization curve, a first spontaneous electrode potential detecting means for detecting the spontaneous electrode potential of the coated metallic material and a substrate metal spontaneous electrode potential signal inputting means are connected to a calculating or processor means which feeds a displaying means to display the corrosion form.

As for further advantages, the judgement of the existence of the metal-plated layer can be performed by the peak detecting means' detection of the peak portion in the anodic polarization curve. Also, if the signal representing corrosion current is input to the processor means, the corrosion form can be stereoscopically displayed on the displaying means.

Furthermore, the peak potential, current and/or area signal determined by the use of the cathodic polarization curve and/or the quantity of electricity of the second peak and its subsequent portion relating to the electrolysis current variation or the quantity of electricity of the third peak can be input to the processor means. This permits a more detailed display of the corrosion-form, as for information on the rust width or pitting depth.

The invention includes a method and its apparatus to measure the corrosion preventing performance of the film in the corrosive gas, steam, soil and non-electrolytes such as crude oil. This is achieved by contacting an alkaline solution with the non-film face opposite to the film side. If the non-film face is potentiostatically electrolyzed, the corrosion reaction on the film side can be estimated by obtaining and using the hydrogen-ionized electrolysis current information (the electrolysis current caused by the ionization of the hydrogen).

As is clear from the description in the foregoing, the present invention has already established a method for detecting significant electrochemical information for corrosion evaluation of a coated metallic material and discloses an apparatus for automatically performing the detecting method described above. Thus, the present invention makes it possible to quantitatively treat the corrosion evaluation of the coated material.

BRIEF DESCRIPTION OF THE DRAWINGS

These and other objects and features of the present invention will become apparent from the following description taken in conjunction with the preferred embodiment thereof with reference to the accompanying drawings in which:

FIG. 1 is a block diagram of a corrosion evaluation testing apparatus according to the present invention, which is used for embodying a method of the present invention;

FIG. 2 is a schematic, cross-sectional view of paired measuring cells according to the present invention which is suitable for use in the measuring cell of the apparatus of FIG. 1;

FIG. 3 is a principle view diagrammatically showing an apparatus according to the present invention which make a film side of a coated metallic material to be first potentiostatically electrolyzed at the spontaneous electrode potential and then to be polarized through the linear potential sweep method;

FIG. 4 is a block diagram of an apparatus which is arranged to automatically perform the operation proposed by the apparatus-principle shown in FIG. 3;

FIG. 5 is a circuit diagram of the apparatus of FIG. 4;

FIG. 6 is a circuit diagram of a detecting apparatus for detecting corrosion current and corrosion potential according to the present invention;

FIG. 7 is a graph illustrating a method of obtaining the corrosion current and corrosion potential according to the present invention, while the method is substantially different from the method adopted for the embodiment of FIG. 6;

FIG. 8 is a principle-diagram of an apparatus for potentiostatically electrolyzing a non-film side of the coated metallic material at a spontaneous electrode potential;

FIG. 9 is a circuit diagram of an apparatus which can automatically perform the principle proposed in FIG. 8;

FIGS. 10(a) and 10(b) are a practical operating flow chart of the apparatus of FIG. 1 while especially specifying the relationship among data (1) to data (21);

FIGS. 11(a) and 11(b) are a flow chart for stereoscopically drawing a corrosion sectional model diagram;

FIG. 12 is a chart illustrating respective pulse wave forms of a train of pulses which are used in the pulse polarization method according to the present invention;

FIG. 13 is a chart illustrating respective pulse wave forms of a train of current pulses which are obtained through the use of the train of pulse potential of FIG. 12;

FIG. 14 is a graph showing the variation in the potential applied with respect to time, which is used in the linear potential sweep method;

FIG. 15 is a graph showing the variation in the polarization current correspondingly caused in accordance with the variation in the potential of FIG. 14;

FIG. 16 is a graph showing the variation in extremely small amount of current-potential (the principle to obtain the real relationship between current and potential by eliminating the ohmic drop);

FIG. 17 is a graph showing the variation in a cathodic polarization curve obtained in the method according to the present invention;

FIG. 18 and FIG. 19 are graphs each illustrating a method for obtaining the peak area of a cathodic polarization curve;

FIG. 20 is a partial view schematically illustrating a defect portion sectional model in a case where the corrosion form is "pitting";

FIG. 21 is a partial view schematically illustrating a defect portion sectional model in a case where the corrosion form is "crevice";

FIG. 22 is an illustrating view showing an embodiment of the method according to the present invention;

FIG. 23 is a graph showing cathodic polarization curves with an immersing time being chosen as the parameter according to an EMBODIMENT 1 of the present invention;

FIG. 24 is a cross-sectional view schematically showing the corrosion form in the film defect portion (wherein dotted lines show a pitting and solid lines show the lateral expanse of a rust width or a crevice corrosion);

FIG. 25 is a graph correlating among the aging variation in peak potential, the aging variation in rust width (X mark), and film peeled-off width (O mark) with respect to the cathodic potential according to the EMBODIMENT 1 of FIG. 23;

FIG. 26 is a graph showing one (immersing time: 500 hours) of the cathodic polarization curves of specimen steel plates A and B according to an EMBODIMENT 2 of the present invention;

FIG. 27 is a graph showing the aging variation in the peak potential with respect to the immersing time according to the EMBODIMENT 2 of FIG. 26;

FIG. 28 is a graph showing the aging variation in the rust width with respect to the immersing time according to the EMBODIMENT 2 of FIG. 26;

FIG. 29 is a graph showing one (immersing time: 100 hours) of the cathodic polarization curves of specimen steel pipes C and D according to an EMBODIMENT 3 of the present invention;

FIG. 30 is a graph showing the aging variation in the corrosion current in the EMBODIMENT 3 of FIG. 29;

FIG. 31 is a graph showing the aging variation in the peak current in the EMBODIMENT 3 of FIG. 29;

FIG. 32 is a graph showing the aging variation in the rust width in the EMBODIMENT 3 of FIG. 29;

FIG. 33 is a graph showing one (immersing time: 20 hours) of the cathodic polarization curves of specimen plates E, F and F' according to an EMBODIMENT 4 of the present invention;

FIG. 34 is a graph showing the aging variation in the rust width in the EMBODIMENT 4 of FIG. 33;

FIG. 35 is a graph showing the aging variation in the peak potential in the EMBODIMENT 4 of FIG. 33;

FIGS. 36(a) and 36(b) are graphs each showing the cathodic, FIG. 36(a), and anodic, FIG. 36(b), polarization curves of specimen plates G and H for an immersing time of 250 hours according to an EMBODIMENT 5 of the present invention;

FIG. 37 is a graph showing the aging variation of the rust width in the EMBODIMENT 5 of FIGS. 36(a) and 36(b);

FIG. 38 is a graph showing the aging variation of peak potential in the EMBODIMENT 5 of FIGS. 36(a) and 36(b);

FIG. 39 is graph showing the cathodic polarization curve of specimen plate H according to an EMBODIMENT 6 of the present invention, while the immersing time is chosen as the parameter;

FIG. 40 is a graph showing the cathodic polarization curve of a specimen plate I according to the EMBODIMENT 6 of the present invention, while the immersing time is chosen as the parameter;

FIG. 41 is a graph showing an anodic polarization curve of the specimen plate I in the EMBODIMENT 6 of FIG. 39;

FIG. 42 is a view for schematically illustrating a normal clearance corrosion form;

FIG. 43 is a view for illustrating the corrosion form according to the present invention;

FIGS. 44 and 45 are graphs each showing the aging variation in an electrolysis current measured with respect to the immersing time according to the present invention;

FIGS. 46, 47 and 48 are graphs each showing the comparison between filiform corrosion length and hydrogen concentration melted in a steel substrate due to corrosion to be effected on the film face side; the corrosion width of the crevice corrosion and the above-described hydrogen concentration; and the depth of the pitting and the above-described hydrogen concentration;

FIG. 49 is a graph showing the aging variation in the electrolysis current measure with respect to the immersing time according to the present invention; and FIG. 50 is a block diagram of an apparatus for detecting the existence of the peak in the electrolysis current variation and the area of the peak.

Before the description of the present invention proceeds, it is to be noted that like parts are designated by like reference numerals throughout several views of the accompanying drawings, unless otherwise denoted.

DETAILED DESCRIPTION OF THE INVENTION

Referring now to FIG. 1; there is shown a block diagram of an apparatus according to the present invention for determining the corrosion state of a film coated metal. A film coated metallic plate W is firmly held between two measuring cells 1 and 1'. One face of the metallic plate W is coated with a film of paint P, while the other face thereof is not coated with paint. A corrosive medium such as a 3% by weight NaCl solution fills the left-hand measuring cell 1, coming in contact with the film face side of the coated metallic plate W. On the other hand, for example, an alkaline solution low in hydrogen ion concentration fills the right-hand side measuring cell 1', contacting the non-film side of the metallic plate W.

A reference electrode R and a counter-electrode C are immersed in the measuring cell 1. To obtain a polarization curve by a linear potential sweep method after the film side is potentiostatically electrolyzed at the spontaneous electrode potential, the electrodes R and C together with a lead from the coated metallic plate W are respectively connected to a potentiostat 2 to form a film side measuring system (hereinafter referred to as an anodic reaction measuring system).

A reference electrode R' and a counter-electrode C' are immersed into the measuring cell 1'. To measure the electrolysis current caused by electrolyzing the non-film side of plate W at a hydrogen ionization electrode potential after the non-film side has been potentiostatically electrolyzed at the spontaneous electrode potential, the electrodes R' and C' and a lead from the coated metallic plate W are respectively connected with a potentiostat 2' to form a non-film side measuring system (hereinafter referred to as a cathodic reaction measuring system).

In the anodic reaction measuring system, a spontaneous electrode potential detecting circuit 3 is connected with the potentiostat 2. A signal which is opposite in polarity, but of the same absolute value as the potential signal output from detecting circuit 3 is transmitted by an auto-set circuit 4 to the potentiostat 2 so that the coated metallic plate W is potentiostatically electrolyzed at the spontaneous electrode potential by the electrostat 2.

Also, a pulse potential generating circuit 5 is connected with the potentiostat 2 to obtain information on the electric resistance of the film for use in detecting film detects. Circuit 5's pulses of potential are applied to the coated metallic plate W after it has been potentiostaticly electrolyzed at the spontaneous electrode potential detected by circuit 3. In addition, a linear potential applying circuit 6 is connected with the potentiostat 2 to cause sweep polarization of the coated metallic plate W at a given potential sweep rate.

Pulse currents from the potentiostat 2 are input to an electrolysis current detecting circuit 7 and then to a pulse current storing circuit 8. The pulse currents are those flowing between the counter-electrode and the coated metallic plate W when the coated metallic plate W is pulse-polarized by a train of pulse potentials originating at the pulse potential generating circuit 5. Cathodic and anodic pulse potentials, each having the same absolute value, are alternately applied to the coated metallic plate W. The corresponding detected cathodic and anodic pulse current signals also are fed to a pulse current value comparing circuit 9 which determines whether or not the film face of the coated metallic plate W is damaged. Film defect detecting signals are output from the comparing circuit 9. Circuit 9 determines that no defects exist when either the absolute values of the acthodic and anodic pulse currents themselves or the two (i.e., cathodic, anodic) values of the electric resistance of the film that can be calculated from the pulse currents, are within 20% of each other. However, it is determined that defects exist when the two calculated values of the electric resistance differ by more than 20%.

Also, according to a linear potential sweep method which is described hereinafter in detail, no defects are determined to exist when the relationship (E vs. i) is approximately linear, while defects are determined to exist when there is a large deviation from the (E vs. i) linear relationship (that is, if "a" is calculated from i=aE, and the variation in "a" over the E vs. i curve is ±10% or more).

Using the pulse polarization method of the present invention, both the electric resistance of the film and the water permeation rate of the film can be both detected. Accordingly, a film electric resistance detecting circuit 10 and a water permeation rate detecting circuit 11 are both provided.

Also, polarization currents from the potentiostat 2, arising due to the potential sweep applied to the coated metallic plate W, are input from the electrolysis current detecting circuit 7 to a current peak detecting circuit 12 and an (E vs. i) storing circuit 13 and an (E vs. log i) storing circuit 14. The peak detecting circuit 12 may be composed of a differentiation circuit. Upon the peak detecting circuit 12's detection of a peak portion in the polarization curve, a detecting circuit 15 detects the peak potential and/or the current at this time. Furthermore, the signal from the peak detecting circuit 12 indicating that a peak has been detected is sent to a peak area detecting circuit 16 to actuate a circuit 16 which detects the peak area from the (E vs. log i) polarization curve, stored in circuit 14. A detecting circuit 17 detects both corrosion currents and corrosion potentials from the (E vs. log i) polarization curve stored in circuit 14.

In response to and output signal from the electric resistance detecting circuit 10, resistance detecting circuit 26 detects a polarization resistance (or an electric resistance of paint film) from the (E vs. i) polarization curve stored in (E vs. i) storing circuit 13.

Lastly, a potential signal from the electrode potential detecting circuit 3 is once stored in a spontaneous electrode potential storing circuit 18 and is compared with the spontaneous electrode potential of a substrate metal, such as iron, by a comparing circuit 19, whereby the comparing signal is output.

In the cathodic reaction measuring system, an electrolysis current detecting circuit 7' is connected with the potentiostat 2'. Detecting circuit 7' feeds a hydrogen electrolysis current signal to a storing circuit 21 and a "second peak" detecting circuit 22. Second peak detecting circuit 22 detects the existence of the second peak in accordance with the aging variation of the electrolysis current, in other words, the quantity of electricity of the second peak. Furthermore, circuit 7' feeds the electrolysis current signal to a "third peak" detecting circuit 23 to detect the rise time of the third peak, in other words, the quantity of electricity of the third peak.

Each of the detected signals in once input to a processor circuit 20 whose output goes to an operation circuit 24 which feeds a display circuit 25 for collectively displaying the corrosion condition, including the corrosion form, of the coated metal specimen W.

Each of the circuit means described above will be further specifically described below. As far as the polarization measurement cell is concerned, one composed of the measuring cells 1 and 1' whose construction is shown in FIG. 2 is preferable. Cells 1 and 1' are respectively composed of a left-hand cell chamber 101 and a similar right hand cell chamber 102. Specimen W has a face side (left-hand side) and a rear side (right-hand side). Specimen W's measuring face side (the left-hand side in FIG. 2) is protected with a silicon rubber elastic insulating plate 103 having a punched opening A of the same area as the measuring face. Specimen W's rear side (the right-hand side in FIG. 2) is also protected with an elastic insulating plate 104, having a punched opening B of the same size as or larger than the measuring face in area. The exterior side (the sides-facing away from plate W) of each plate 103 and 104 is respectively pressed by a flange portion 101a, provided for the left-hand cell chamnber 101, and a flange portion 102a, provided for the right-hand cell chamber 102. The two flange portions are clasped towards each other by a grasping means (not shown), so that the both chambers are fixedly assembled as shown in FIG. 2.

The left-hand side cell chamber 101 has a first trough-like tube 105 and a second trough-like tube 106 on its top face. The first tube 105 allows the reference electrode R to be set in the chamber. The reference electrode R has to indicate the stable electrode potential and may be a calomel electrode, silver-silver chloride electrode or the like. The second tube 106 allows the counter-electrode C, which can be of platinum, silver, carbon or the like, to be inserted into chamber 101. Alternatively, the counter-electrode C and the reference electrode R can be installed together in first tube 105, eliminating the second tube 106. There is no adverse influence upon the measured value even if the reference electrode R and the counter-electrode C are placed near each other. In addition, a helically formed heating tube 107 is provided in the chamber 101. A given amount of warm water is continuously fed into heating tube 107 from an entrance 107a and discharged at an exit 107b each located in one end face of the chamber 101. In this way the electrolyte in chamber 101 may be kept in a predetermined temperature condition.

Since cell chamber 102 on the right-hand side is approximately a mirror image of cell chamber 101, like parts are designated by the same reference numerals. The left-hand side cell chamber 101 is filled with an NaCl solution of a predetermined concentration, while the right-hand side cell chamber 102 is filled with an NaOH solution of a predetermined concentration. In left-hand side cell 1, electrolysis which confirms the polarization behavior of the film side or coated side of the coated metallic plate W is performed. In right hand side cell 102, hydrogen electrolysis of the non-film face side is performed.

The advantages of using the present measuring cells 101 and 102 are as follows:

(1) The measuring area or exposed area can be precisely and easily set by the determination of the area of the punched opening A, and the measured values can be correctly compared with respect to each other.

(2) The solutions filling in the measuring cells 101 and 102 can be of different temperatures to perform accelerated tests under a thermal gradient condition.

(3) Since the electrolytic cells 101 and 102 are separated by insulating materials 103 and 104, the cathodic reaction and the anodic reaction with respect to the coated metallic plate W can be traced with a single compact unit.

(4) Since an alkali solution, such as NaOH solution or the like fills cell 102, the behavior of the electrolysis on the non-coated face side does not influence the corrosion behavior on the coated face side.

(5) There is no short circuit between the solutions of measuring cells 101 and 102.

To polarize the plate W's coated face side by the linear potential sweep method after the coated face side is potentiostaticly electrolyzed at the spontaneous electrode potential, an apparatus such as shown in FIG. 3 is used. Reference electrode R is connected in series with a variable potential battery V and an amplifier AMP. The output side of the AMP is connected to counter-electrode C through an ammeter A. The output side of the ammeter A is connected to a reading means B for reading the changes in current. For example, means B may be a recording meter or a computer means, a logarithmic transducer or the like. Also, to obtain the potential difference between the reference electrode R and the coated metallic plate W, the plate W can be grounded and a voltmeter E connected between the reference electrode R and the grounding member. The output of voltmeter E is connected to a recording meter B', it may also be connected to reading means B so that means B can read and display how the variation potential E affects in the logarithmic value of the current i (E vs. log. i).

Upon polarizing the coated metallic plate W, the potential difference (Eo) between the reference electrode R and the coated metallic plate W is first measured and then the output of the battery V is adjusted to cause a cancelling (−Eo) drop between electrode R and input "a" of the AMP so that the potential difference between the inputs (a—b) of the AMP is approximately zero. Since the output of the AMP becomes approximately zero through this adjustment, no current flows to the counter electrode C. Nor does much current flow to the coated metallic plate W. Thus, the potentiostatic electrolysis can be said to be performed at the spontaneous electrode potential.

After setting the spontaneous electrode potential as described above, the potential-variable battery V is adjusted. The coated metallic plate W is polarized in accordance with the changes in potential with a given potential sweep rate (potential variation Δv/(time variation)Δt) to provide the polarization curve of the coated metallic plate W, particularly the cathodic polarization curve. Owing to the potentiostatic electrolysis of the coated metallic plate W at the spontaneous electrode potential as described above, any measuring current error relating to a polarizing current caused by a difference in the spontaneous electrode potentials between the coated metallic plate W and the counter-electrode C is well prevented from flowing. When film defects exist, the polarization currents related to the defect regions are larger than that related to the other film portions. Therefore, the polarization current in the other film portion can be eliminated from the measured value.

FIGS. 4 and 5 show an apparatus, based upon the measuring principle shown in FIG. 3, for automatically polarizing the coated metallic plate W having slight film defects, after the plate W is potentiostatically electrolyzed at the spontaneous electrode potential.

A means 202 for measuring electrode potentials comprises a high impedance operational amplifier 203 (see FIG. 5) and a voltmeter 216 (see FIG. 5) as shown in FIGS. 4 and 5. The high impedance operational amplifier 203 has an input resistance ($10^{14}\Omega$ or more) sufficiently higher than the film resistance between the coated metallic plate W and the reference electrode R. The voltmeter 216 (see FIG. 5) is connected to the reference electrode R through the high impedance operational amplifier 203 at one end and the grounding member at the other. Due to this arrangement the electrolysis current caused by the application of the electrical potential is caused not to be input to the means 202 in any way so as to be able to correctly measure the variation of the spontaneous electrode potential of the coated metallic plate W.

An electrode potential auto-set circuit 204 approximately sets the currents caused by any difference in the electrode potentials between the electrode C and the plate W to zero so that the plate W is electrolyzed at the spontaneous electrode potentials in the corrosive solution. Circuit 204 comprises a servomechanism 208, a first differential amplifier 205 and a compensation means 206 for imparting a compensation signal. More specifically, the servomechanism 208 is connected in parallel to the first differential amplifier 205 (see FIG. 4) and in series to the amplifier 203 (see FIG. 5). The output voltage of means 206 (see FIG. 5) is set with the help of the servomechanism 208. Further description will be given hereinafter with reference FIG. 5. One input of first differential operational amplifier 205 receives the output of high impedance operational amplifier 203 and the other input of amplifier 205 receives the output of the slider of potentiometer P1 of the means 206. The output current of amplifier 205 is fed to counter-electrode C to operate to cancel the output (potential signal) from the amplifier 203 and the output (compensation signal) from means 206 to approximately zero the error currents effected by the differences in the electrode potentials between the coated metallic plate W and the counter electrode C.

The means 206 (see FIGS. 4 and 5) for imparting a compensation signal comprises the potentiometer P1, a DC power supply E1 and a distributed resistor R9 and R10, these being connected in parallel with respect to each other and grounded through a normally open contact L6 from a junction point between resistors R9 and R10. The means 206 is connected on its output side through the potentiometer P1 to the differential operational amplifier 205 and is grounded through a normally closed contact L7. Such being the case, in a case where the contact L7 is in its ON mode (closed mode), no compensation signal is input to the differential operational amplifier 205. But when contact L7 is in its OFF mode (open mode) and normally open contact L6 is simultaneously in its ON mode (closed mode), a compensation signal is input to the differential operational amplifier 205.

Furthermore, the servomechanism 208 comprises a comparator 209, a servomotor 210 and a comparison signal means 211 constituting a negative feedback circuit. Comparator 209 is a servo amplifier whose to inputs are the output of amplifier 203 and the comparison signal means 211. The output of comparator 209 leads to servomotor 210 through a normally open contact L0 (see FIG. 5). Comparator 209 compares amplifier 203's output (potential signal) with the voltage developed by comparison signal means 211 and outputs their difference as a signal, to drive the servomotor 210 when contact L0 is closed.

The comparison signal means 211 (see FIGS. 4 and 5) comprises a potentiometer P2, a DC power supply E2 and a distributed resistor R7 and R8 connected in parallel. A junction point between resistors R7 and R8 is grounded. Means 211 is connected through the slider of potentiometer P2 to an input of comparator 209 to input comparison signals. In addition, the servomotor 210 is adapted to simultaneously move potentiometer P1 of means 206 and potentiometer P2 of means 211. Servomotor 210 is driven by comparator 209 to set a compensation signal capable of cancelling the potential signal described above with the potential signal itself. To retain the established compensation signal, normally open contact L0 is switched from ON to OFF to cut off the input from comparator 209 to the servomotor 210.

First the above-described measuring preparation is performed under the above-described construction. Then, a power supply 207 causes application of a low DC cathodic or anodic voltage gradient between the coated metallic plate W and the reference electrode R. Power supply 207 comprises a potentiometer P3, a DC power supply source E3, and a distributed resistor R11, and R12 connected in parallel. Pontetiometer P3's slider is connected via a contact L8 to the junction point of resistors R9, R10 of means 206, imparting a comparison signal whenever a normally open contact L8 is closed. The junction point between resistors R11, R12 is grounded. Accordingly, a low DC voltage of positive or negative gradient is output from the power supply 207 by movement of potentiometer P3 and superimposed upon the compensation signal being developed at means 206 for input to first differential operational amplifier 205. And it comes to the counter-electrode C to apply the output potential between the coated metallic plate W and the reference electrode R.

Still referring to both FIGS. 4 and 5, an apparatus 212 (see FIG. 4) for measuring a very small amount of polarization currents flowing through the film defect portion includes a second differential operational amplifier 217 and a corrector means 218 (see FIG. 5) for imparting a correction signal. More specifically, amplifier 217 is connected in parallel with a variable resistor R7. One of amplifier 217's inputs receives the output of an amplifier 214. The input of amplifier 214 is connected to the coated metallic plate and amplifier 214's output side is grounded through an ammeter 220.

Referring back to FIG. 5, a numeral 213 designates a multistage parallel resistor wherein resistors R1 to R4 are each respectively connected in series with a normally open contact L1 to L4, and resistor R5 is connected in series with a normally closed contact L5, the five resistor-contact branches are connected in parallel. Thus by changing which contact is switched closed, the resistance in series with electrode C can be controlled.

Corrector means 218 comprises a potentiometer P4, a DC power supply E4 and a distributed resistor R13 and R14 in parallel. The slider of potentiometer P4 contacts to one of the inputs of second differential operational unit 217. The junction point between resistors R13 and R14 is grounded.

Potentiometer P3 of power supply 207 and potentiometer P4 of corrector means 218 are adapted to be simultaneously moved at a given speed by a synchronous motor 219. As described hereinbelow, the synchronous motor 219 is driven so that a low DC voltage of positive and negative gradient is applied between the counter-electrode C and the reference electrode R. The corresponding variations of the electrolysis currents responsive to the external polarization signal on plate W is input to the amplifier 214. These currents are amplified and input, as the measuring signal, to the second differential operating unit 217. On the other hand, in corrector means 218 the output voltage of the DC power supply E4 is synchronized to vary with the same gradient as that of the low DC voltage applied due to the movement of the potentiometer P3. The potential output from E4 is input as a correction signal to unit 217 which outputs a difference signal to the ammeter 220 to compare the currents flowing over the film portion to measure the current signal flowing only into the defect portion of the film. Also, if E4 is arranged so that the current-potential gradient specific to the film's electric resistance when undamaged is shown as a correction signal by the displacement of potentiometer P4, the difference in external polarization current before and after the film becomes damaged can be detected. Also, in the above-described apparatus, the current value showing the electric resistance specific to the film resistance is adapted to be compensated. However, when the currents flowing over the film defect portion are sufficiently larger than the currents flowing into the film portion (for example, approximately 100 times can be neglected), the measurement can be directly made through the second differential operational amplifier 217 by ammeter 215, connected at one end to amplifier 214 and grounded at its other end by opening contact L10 without obtaining the external polarization currents of the film defect portion.

Then, the operational characteristics of the polarization current measuring apparatus, of the film defect portion, under the above-described construction will be in sequence described hereinafter.

All contacts are opened. The spontaneous electrode potential of the coated metallic plate W is measured by the spontaneous electrode potential measuring means 202.

More particularly, the electrode potential (spontaneous electrode potential) with respect to the reference electrode R of the coated metallic plate W is output to the voltmeter 216 through the high impedance operational amplifier 203, so that the variation of the spontaneous electrode potential is recorded.

Successively, the contacts L6 and L0 are closed, thereby to operate the auto-set circuit 204 of the electrode potential (FIG. 4), so that the currents caused by the difference of the electrode potential between the coated metallic plate W and the counter-electrode C are then set to approximate zero. Namely, the output (potential signal) of the high impedance operational amplifier 203 is input to the first operational unit 205 and to the comparator 209. The comparison signal which supplies a voltage −Vs cancelling the potential signal is, first, input to the comparator 209. The compensating signal −Vs is kept inputted even to the first operational unit 205. No output is provided from the comparator 209. The output of the first operational unit 205 does not exist with the servomotor 210 being in an OFF mode.

Assume that the coated metallic plate W has been corroded and the electrode potential has risen an amount $\Delta V$ to $Vs+\Delta V$. Such being the case, the potential signal $(Vs+\Delta V)$ is input from amplifier 203 to the first operational unit 205 and the comparator 209. The difference portion $\Delta V$ with respect to the comparison signal output from the comparator 209 as well as from the first operational unit 205. However, the signal $\Delta V$ from the comparator 209 is input to the servomotor 210. The servomotor 210 is driven to displace the potentiometers P1 and P2 to output the comparison signal of $-(Vs+\Delta V)$ from the means 211 which is input to the comparator 209 to zero the output of 209. Upon suspension of the driving operation of the servomotor 210, a compensation signal of the $-(Vs+\Delta V)$ is output from the means for imparting a compensation signal 206 and then is input to the operational unit 205 to cancel the input of the potential signal from amplifier 203, whereby the output of the operational unit 205 becomes zero.

Accordingly, the current (error current), which tends to flow between the coated metallic plate W and the counter-electrode C is set spproximately to zero. Thus, according to the present invention, the coated metallic plate W is electrolyzed at the spontaneous electrode potential of the coated metallic plate.

After the measuring preparation described above is finished, contacts L0 and L6 are both opened, and the contact L8 is closed. Thus, the potentiometer P3 of the power supply source 207 is displaced by the synchronous motor 219 and then the potential applied is varied, with the cathodic or anodic gradient of the potential being accompanied. Hence, the current flowing between the coated metallic plate W and the counter electrode C is input to the second operational unit 217 on one hand and the correction signal is input to the second operational unit 217 from the means 218 provided with the potentiometer P4, which is simultaneously displaced by the synchronous motor 219 on the other hand. The difference in the currents $\Delta i$ between the measuring signal i and the compensation signal is successively output and then amplified so as to be measured by the ammeter 220.

According to a further detailed description, when the contact L0 is open, the connection between the comparator 209 and the servomotor 210 is cut off according to the present invention. Hence, the current caused by the DC voltage power source is not to be input to the servomotor 210, whereby the voltage of the compensation signal is retained in order to prevent the electrolyzing condition at the spontaneous electrode potential from being deviated. Then, when the contact L6 is opened and the contact L8 is closed, a predetermined potential is applied between the counter-electrode C and the reference electrode R.

Thereafter, in accordance with the drive of the synchronous motor 219 and the displacement of the potentiometer P3 in the direction of A in FIG. 5, the application of potential increases with the positive gradient of the potential, whereby the current signal of $-i$ of an anodic external polarization curve of the coated metallic plate W is adapted to be input to the second operational unit 217. On the other hand, when the potentiometer P3 is displaced in the direction of B in FIG. 5, the application potential decreases with the negative gradient of the potential, whereby the current signal of $+i$ of the cathodic external polarization curve of the coated metallic plate W is input to the second operational unit 217.

The synchronous motor 219 is driven so as to cause the potentiometer P4 of the means 218 for imparting a correction signal to be displaced in the A' direction in synchronization with the displacement of the potentiometer P3 in the A direction. On the contrary, the potentiometer P4 is displaced in the B' direction in synchronization with the displacement of the potentiometer P3 in the B direction. The DC power supply source E4 is set so that the currents (correction signal) of the current-potential with a predetermined gradient, which is obtained through application of the potential variation from the application voltage supplying means upon the pre-measured film resistance, may be supplied by the displacement of the potentiometer P4. Accordingly, a correction signal is input to the secondary operational unit 217 from the means 218 for imparting a correction signal. The difference current $\Delta i$, in which a correction signal (the correction signal is input to the second operational unit 217 as the voltage signal, and the film resistance value is converted to a current value within the unit 217) corresponding to the film resistance from the current signal $\pm i$ of the anodic or cathodic external polarization curve is subtracted, is output from the second operational unit 217 and is measured by the ammeter 220. When the current signal $\Delta i$ is recorded and correlated with the electrode potential of the coated metallic plate W, the intended polarization curve relating to the defect portion of the very small amount of film defects of the coated metallic plate W is provided.

According to the present invention, the above-described apparatus is also provided with a function of measuring the electric resistance of the film of the coated metallic plate W. After the operation of the potentiostatic electrolysis (measuring preparation) at the spontaneous electrode potential, the electric resistance of the film is obtained by the pulse polarization method with the sufficiently correct measured value being guaranteed even if the voltage is rendered low enough not to disturb the measuring system.

Namely, referring to FIGS. 4 and 5, after the measuring preparation as described above, a contact L9 is closed with the contacts L0 and L6 being simultaneously opened, thereby to supply the pulse signal from a pulse power supply source 207a to measure the electric resistance of the film by the electrolysis current measuring means 212 (see FIG. 4).

First, open the contact L0 and break the connection between the comparator 209 and the servomotor 210, thereby to prevent the pulse signal from being input to the servomotor 210 halting its resultant error operation. If the pulse signal were input to the servomotor 210, a compensation signal cancelling the pulse signal would be output, with the result that the electrolysis current as the signal of the electric resistance of the film would not be available. Thereafter one outputs a pulse signal VP from the pulse power supply source 207a, whereby the pulse signal VP is superimposed upon the compensation signal of means 206 input to the operational unit 205. However, since the compensation signal of means 206 is cancelled by the potential signal from amplifier 203 as described above, only the net pulse signal is output from the operational unit 205 to counter-electrode C.

Such being the case, the voltage pulse VP from unit 205 properly dropped by the multistage resistor 213, is applied between the reference electrode R and the counter-electrode C. The electrolysis current signal, responsive to pulse VP, flowing between the counter-electrode C and the coated metallic plate W is amplified by the amplifier 214 and is measured by the ammeter 215 for recording. Since the potential of this pulse signal is set sufficiently small, in comparison with the spontaneous electrode potential of the coated metallic plate, no adverse influence is applied to the spontaneous electrode potential. Therefore, the spontaneous electrode potential of the coated metallic plate can be measured in conjunction with application of a continuous series of resistance measuring pulse signals. If desired, the pulse signals of one polarity described above may be alternated with those of an opposite polarity or the application wave of the potential may take the stagewise forms. Thus, for example, the difference in DC resistance corresponding to the difference in current direction in the coated metallic plate can be easily detected.

Also, in the above-described contact switching operation, to measure the electrode potential of the coated metallic plate W, the contacts L5 and L7 are first opened from a time $t_0$ to a time $t_1$. Then, from a time $t_1$ to a time $t_2$, the contacts L0, L5 and L6 are closed to set the error currents, due to the difference in the electrode potential between the coated metallic plate W and the counter-electrode C, to an approximately zero. In this way the measuring preparation of the electric resistance of the film for electrolyzing the coated metallic plate at the spontaneous electrode is successively performed. Then, from time $t_2$ to a time $t_5$, contacts L0 and L6 are opened and contact L9 is simultaneously closed. A pulse potential of the $+V_p$ is applied from time $t_2$ to a time $t_3$ and a pulse potential $-V_p$ is applied from a time $t_4$ to a time $t_5$ to measure corresponding electrolysis currents $i_p$ and $-i_p$ flowing between the coated metallic plate W and the counter-electrode C. When the these steps are compiled into a program and repeatedly performed both the spontaneous electrode potential and the electric resistance of the film can be automatically measured for a long period during which the electrolysis operation is performed at the spontaneous electrode potential.

The detecting circuit 17 for detecting corrosion currents and corrosion potentials may be constructed as shown in FIG. 6.

Referring to FIG. 6, numeral 1 designates the measuring cell. In the cell 1 is a specimen plate W, coated on its surface by a resin film containing inorganic or organic substance, and that is plate partially injured with a sharp blade. The reference electrode R is one which has a stable electrode potential, such as the calomel electrode, silver-silver chloride electrode or the like. The counter-electrode C is an uncoated metallic plate of platinum or the like. Plate W and electrodes R and C are immersed in a corrosive solution, such as a 3 to 5 percent salt solution or the like.

Numeral 302 designates a means which electrolyzes the specimen plate W at the spontaneous electrode potential while setting the error currents, which lead to measuring errors, to zero. Means 302 substantially comprises an operational amplifier 303. As shown in FIG. 6, a DC power supply source E1, grounded at its one end through a switch SW1, is connected to one input of the operational amplifier 303 through a potentiometer P1. Reference electrode R is connected to the other input of amplifier 303. The counter-electrode C is connected through an appropriate variable resistor Ro to the output of amplifier 303. The electrode potential difference of the specimen W with reference to the reference electrode R indicated by a voltmeter 304 grounded at its one end. By the arrangement described above, a voltage of polarity opposite to the potential shown by meter 304 is input to the operational amplifier 303 from P1 by adjustment of potentiometer P1 to zero the output of amplifier 303 so that the very small amount of polarization currents during application of the low-leveled potential can be correctly measured.

Numeral 306 designates a means for applying a linearly increasing excessive potential to specimen W to polarize it. Means 306 comprises a DC power supply source E3, a potentiometer P3, a switch SW3 and an integration circuit 307. One end of the DC power supply source E3 is grounded and its other end is connected to the integration circuit 307 through potentiometer P3 and switch SW3. The output of integrator 307 is connected to a contact (c') of switch SW1 so that by a change-over operation of switch SW1 an output voltage which is gradually being increased by the integration circuit 307 can be added to the output voltage produced at P1's slider by source E1.

Numeral 308 designates a means for applying a slight excessive potential ranging from 0 to 10 mV upon the coated metallic plate W. Means 308 comprises a DC power supply source E4 connected to a contact (b') of switch SW1 through a potentiometer P4. Thus, the slightly excessive potential or voltage described above can be applied upon the coated metallic plate W through a change-over operation of the switch SW1 to (b'). Hence, the predetermination of the degree of the proper current amplification in accordance with the maximum polarization current during the measurement of the corrosion current is arranged to be easily accomplished. Namely, when a polarization current of approximately 100 times is adapted to flow upon the measurement of the polarization current during application of 10 mV, it is observed that almost all the specimens W are polarized to a range sufficient to obtain a Tafel slope, whereby the polarization current which becomes a reference for obtaining the maximum polarization current value is provided.

Numeral 309 designates a comparator circuit, which has a first input connected to the output side of integration circuit 307 so that the application voltage of integrator 307 may be input to the comparator circuit. A comparison potential of 10 mV feeds a second input of circuit 309. When the difference between these two inputs of circuit 309 has become zero, a signal carrying information of this comparing result is input to a switch SW4 and a holding circuit 311. Circuit 311 is connected, through switch SW4 and a multistage current amplifier 310, to plate W. Therefore, when the specimen plate W becomes polarized at a potential of 10 mV, switch SW4 is opened, while the output voltage of the current amplifier 310 at this time is adapted to be retained in the holding circuit 311.

As is shown in FIG. 6, the specimen W is grounded. Five comparator circuits 312 and 316 are connected in parallel with respect to each other between the counter-electrode C and variable resistor Ro. Each of the comparator circuits 312 and 316 has another input fed from a selected slider point of a multislider potentiometer P5 powered by a comparison-reference power supply source E5. Source E5 corresponds in capacity to the variation in voltage drop IR across variable resistor Ro caused by the polarization current during the final application of potential application means 308. More particularly, when the IR drop is E(V) and the output voltage of the reference power supply source E5 is then set at E(V), the potentiometer P5 is set to give the respective logarithmically equally spaced potentials, 10E(V)/100 for the comparator circuit 312, 17.8E(V)/100 for the comparator circuit 313, 31.6E(V)/100 for the comparator circuit 314, 56.3E(V)/100 for the comparator circuit 315, and 100E(V)/100 for the comparator circuit 316, as the inputs the comparator circuits 312 to 316. Thus, when the IR drop of the resistor Ro caused by the polarization current coincides with another input voltage, a signal is adapted to be imparted. At this time, the input potential to each of the comparator circuits 312 to 316 is fixed. The potential drop by the preferable maximum, polarization current established by the specimen W is to set the resistance value of the variable resistance Ro so that the potential drop may coincide with the output voltage of the reference power supply source E5.

Each output-side of the comparator circuits 312 to 316 is connected to a first input-side of a corresponding holding circuit 318 to 322, while a second input-side of each holding circuits is each connected the counter-electrode R. The coincident signal of each of the comparator circuits is sequently input. The electrode potential difference between the reference electrode R and the specimen plate W at that time is adapted to be sequentially stored and retained in each of the holding circuits 318 to 322.

Meanwhile, each holding circuit 311 and 318 to 322 has a corresponding output connected to a digital panel meter 324 through gate circuit 323 to indicate the voltage at each of the measuring points.

Then, examples where the corrosion currents of various specimen plates are measured by the use of the corrosion current measuring apparatus of the above-described character is detailed hereinbelow.

REFERENCE EXAMPLE 1

The specimen plate was a 7×14×0.08 cm piece of polished steel plate (Japanese Industrial Standards, G.3141) coated with an electrodeposition paint for use in undercoating general vehicle bodies. The electrodeposition paint was substantially composed of a malein oil including a 10 per cent solid stuff and having pH-value of 8. The steel plate was dipped in the paint at 30° C. with a 200 volt DC voltage being applied for three minutes. After coating operation, the plate was washed with water. Subsequently, it was dried at a temperature of 170° C. for thirty minutes to harden the paint. The film thickness was 25 μ.

Successively, the steel plate was injured with a sharp blade to such an extent that the injury extended from the film surface of the coated steel plate to the underlying steel plate itself. By microscopic measurement, the injury was a 10 mm long straight line of $3.2 \times 10^{-2}$ cm$^2$ in area (where the steel was in contact with the liquid). The coated surface was sealed with a water-proof tape with the exception of a 2 cm radius circle enclosing the injured area so that entry of water into the film at places outside the test circle was prevented. This eliminated other possible influences caused by other injuries outside the test circle and effects from the ends of the steel plate and the reverse face of the steel plate. The plate so treated was dipped in the measuring liquid. The measuring liquid employed was a 3 percent NaCl solution at a temperature of 50° C. At the same time a platinum counter-electrode and a saturation calomel (S.C.E.) reference electrode were also dipped in the liquid. The injured coated steel plate was subjected to a linearly applied test voltage at a potential scanning or sweel rate of 50 mV per minute and was polarized. The polarization was a so-called anodic polarization with the current flowing from the specimen to the counter electrode immersed in the liquid. The variation in the current during this polarization was detected and measured.

First, the application of 10 mV was performed upon the specimen plate W by the applying means 308. Measurement of the reference polarization current showed an approximate value of $2.0 \times 10^{-5}$A (amperes). Such being the case, to set a maximum polarization current of $2 \times 10^{-5}$A flowing through the variable resistor Ro as the final measuring point (polarization current equals 100%) the variable resistor Ro was set to $10^5 \Omega$, i.e., the maximum voltage or potential drop across Ro became 2 V. The other lower polarization current values were set at four equally logarithmicly spaces values, the lowest being 10% of the maximum, i.e., the measuring points, $0.2 \times 10^{-5}$A (10%), $0.356 \times 10^{-5}$A (17.8%), $0.632 \times 10^{-5}$A (31.6%) and $1.126 \times 10^{-5}$A (56.3%) correspondingly coinciding with the comparison voltages or potentials divided in advance into the logarithmically equal different spaces.

When the polarization current flowing through resistor Ro is $2 \times 10^{-5}$A, the overpotential was approximately 200 mV. The specimen plate W was polarized to such an extent that the logarithmic values of the overpotential and the polarized current became linear. And the integration circuit 307 was so arranged that the overpotential might be increased with the linear scanning rate of 50 mV per minute.

Next the specimen plate W was immersed in the corrosion liquid for forty eight hours, after which the specimen plate W was anodically polarized from the spontaneous electrode potential by the overpotential applying means 306 while the specimen plate W was being electrolyzed at the spontaneous electrode potential. The polarization current when an overpotential of 10 mV was applied caused a reading of 0.835 V with respect to a full scale of voltage of 1.0 volt on the holding circuit 311. Accordingly, the polarization current difference corresponding to the overpotential difference of 10 mV is $1.67 \times 10^{-7}$A.

In accordance with a further polarization operation of the specimen plate W, the overpotential corresponding to the polarization current at each measuring point was sequentially recorded by holding circuits 318 to 322 as shown in Table 1.

TABLE 1

| Measuring point (%) | Established polarization current value (A) | Holding circuit | Electrode potential of specimen plate (mV) | Overpotential difference (mV) |
|---|---|---|---|---|
| 10 | $0.2 \times 10^{-5}$ | 318 | −505 | |
| 17.8 | $0.365 \times 10^{-5}$ | 319 | −473 | 32 |
| 31.6 | $0.632 \times 10^{-5}$ | 320 | −440 | 33 |
| 56.3 | $1.126 \times 10^{-5}$ | 321 | −403 | 37 |
| 100 | $2 \times 10^{-5}$ | 322 | −367 | 36 |

In respect to the optimum overpotential difference, it was estimated that the values of the overpotential and the logarithmic polarization current were in a linear relationship in the measuring points of 56.3% or more due to a fact that the overpotential difference of 37 mV for the 56.3% measuring point and 36 mV for the 100% measuring point were almost equivalent. Therefore, as far as the optimum overpotential difference between measuring points for this case is concerned, 37 mV was adopted. Since the polarization current measuring points were chosen to divide one logarithmic cycle into four logarithmicly equal divisions as described above, the Tafel slope calculated for a full cycle became a value of 148 mV ($= 37$ mV$\times 4$).

On the other hand, the Tafel slope which was obtained by an extrapolation of the curve of log i vs. E was also 148 mV, wherein the curve described above correlates the logarithmic values of the polarization currents against the respective values of the overpotential and is recorded as a correlation of log i vs E as previously described.

Accordingly, it can be said that the measuring result is sufficiently reliable.

The Tafel coefficient according to the cathodic reaction can be obtained by the following expression for the corrosion current $i_{corr.}$:

$$i_{corr.} = 1/2.3 \cdot (b_a \cdot b_c/b_a + b_c)_c / b_a \cdot \Delta i / \Delta E \tag{1}$$

where $b_a$ is the anodic Tafel coefficient, $b_c$ is the cathodic Tafel coefficient, and $\Delta i$ is the polarization current difference corresponding to overpotential difference $\Delta E$. In this example, the following simplified equation can be used for the estimating the corrosion current:

$$i_{corr.} = b_a 2.3 \cdot \Delta i / \Delta e \tag{2}$$

According to the equation (2), the corrosion current for the present case takes the following value.

$$i_{corr.} = \frac{148 \times 10^{-3}}{2.3} \times \frac{1.67 \times 10^{-7}}{10 \times 10^{-3}} = 1.07 \times 10^{-6} \tag{A}$$

According to the above embodiment, the Tafel slope was obtained by selecting equally logarithmically spaced current points for measurement. On the other hand, the Tafel slope can be obtained with the equally split voltages as a reference.

In this case, the potential is equally divided while being based on $E_{corr.}$ to set equally spaced E1, E2, E2, ... Ex points to detect the corresponding logarithmic values of the polarization currents in each of the points, i.e., log $i_1$, log $i_2$, log $i_3$, ... log $i_x$. Successively, the difference $\theta_1 (= \log i_1 - 0)$, $\theta_2 (= \log i_2 - \log i_1)$ etc. are obtained, whereby when the same difference values are obtained among the neighboring respective gradients (a relative difference of 10% or less is allowed) a Tafel slope can be determined. For example, referring now to the E versus log i plot of FIG. 7, points $\theta_3$ to $\theta_6$ each have approximately the same gradient in the anodic polarization curve on the left. Thus, a line ① extending through the points 2 to 6 becomes the anodic Tafel line of the anode polarization curve for this case. Similarly, in respect to a cathodic polarization curve on the right hand side in FIG. 7, a line ② becomes a cathodic Tafel line. Since the value of the current at the intersection between anodic line 1 and cathodic line 2, corresponds to the corrosion current, $I_{corr}$ can be read out from FIG. 7. As a matter of fact, once both Tafel slopes are obtained, the potential is further divided into potential spaces each being equal as described previously in a direction designated by ⊖ in FIG. 7. The current value of each of potential points thus prepared is calculated by the use of the Tafel slope on the anodic side. Thus, the Tafel line can be extended into the cathodic side. Similarly, the potential is further divided into potential spaces each being equal as described previously in a direction designated by ⊕ in FIG. 7. The current value of each of potential points thus prepared on the cathodic side is calculated by the use of the Tafel slope on the cathodic side. Accordingly, the Tafel (tangential) line is extended into the anodic side. According to the present invention, these two extrapolated current values are compared by the comparator circuit which detects a coinciding value as the corrosion current.

Referring now to FIG. 8, there is shown a principle circuit diagram according to the present invention, wherein the anodic reaction measuring system (film side measuring system) (see FIG. 3) and a cathodic reaction measuring system (non-film side measuring system) are combined. The potentiostat 2' in the cathodic reaction measuring system and the electrolysis current detecting circuit 7' are constructed as shown on the right-hand side of FIG. 8. Namely, the reference electrode R' inserted into the right-hand side measuring cell 1' is connected through the DC power supply source V' to the potentiostat 2'. The output side of the potentiostat 2' is connected, through the electrolysis current detecting circuit 7', to the counter electrode C'. The relative electrode potential on the non-film side face of the coated metallic plate W is set to become approximately zero with respect to the reference electrode by the DC power supply source V', so that the non-film side face may become a condition for atomic hydrogen to be ionized. The initial potential of the non-film side face of the coated metallic plate W is maintained by the potentiostat 2'. Thus, the electrolysis currents caused when the atomic hydrogen is ionized on the non-film side face flow between the coated metallic plate W and the counter electrode C' and are detected by the detecting circuit 7'.

The characteristic features of the present apparatus are described in the following.

(1) Because a constant-potential electrolysis operation is performed with the relative electrode potential of the non-film face of the coated metallic plate W being kept at approximately zero with respect to the reference electrode, atomic hydrogen produced on the film face side and diffusing through the steel to the non-film face side is all ionized on the non-film face and the atomic hydrogen concentration on an interface of the non-film face with the alkaline solution becomes approximately zero. Thus, a concentration gradient of the atomic hydrogen is caused in the steel from the film face to the non-film face. A driving force for the diffusion of the atomic hydrogen through the steel is caused by this concentration gradient and thus, the atomic hydrogen's penetration of the steel can be caused without farcibly polarizing the coated steel plate.

(2) In addition, since the non-film face is in contact with an alkaline solution, $H^+$ ion concentration is small and the atomic hydrogen is highly likely to be ionized.

(3) Furthermore, since the non-film face is in contact with an alkaline solution, the corrosion currents on the non-film face can be controlled. Accordingly, the hydrogen electrolysis current can be correctly measured.

According to the present invention, to automatically set the above-described relative electrode potential on the non-film side face of the coated metallic plate to approximate zero with respect to the reference electrode, portions of the apparatuses described in FIGS. 4 and 5 can be used. The necessary circuit provisions are shown in FIG. 9, wherein the same numerals are used to the same components as those of FIG. 5.

Referring now to FIG. 9, in this figure, when the contacts L0 and L6 are opened and contacts 15 and L7 are closed, operational amplifier 205 outputs the electric power required for causing the electric potential level of the non-film side to be relative zero with respect to the electrode potential of the reference electrode R'. This means that the side reverse to the coated side of the coated metallic plate W, i.e. non-coated or non-film side, is potentiostatically electrolyzed at zero potential with respect to the electrode potential of the reference electrode R'. Thus, if the electrolysis current flowing between the non-coated side and the counter-electrode C' is detected with the help of the means 7' (which substantially comprises a voltmeter), the resultantly detected value itself is the discharged current value of the atomic hydrogen, which is discharged through the substrate metal of the coated specimen plate W. Respective means designated by 206, 209, 210, 211 and their relating means are all prepared for setting the potential level of the non-coated side of the coated specimen plate W at the spontaneous electrode potential.

Referring to FIG. 9, in order to switch over the measuring range subject to the respective magnitudes of the electrolysis currents, a rotary solenoid switch L can be provided capable of being connected to a multistage resistor 213 each of whose various resistors is connected at one end to the output of amplifier 205. By the above arrangement, when the voltage drop $V_0$ of the multistage resistor 213 becomes larger than the output voltage of $V_1$ of a comparision power supply source 221 ($V_0 > V_1$), a comparator 222 outputs a difference signal to amplifier 223 to actuate a relay, whereby the proper switching operation ($L_5$, $L_4$, ... or $L_1$) is correspondingly effected in accordance with the magnitude of the difference signal.

The operation of the corrosion evaluation measuring apparatus according to the present invention, which is shown in FIG. 1, is described hereinafter with reference to FIGS. 10 and 11.

Referring now to FIG. 10, there is shown an operation flow chart wherein the same numerals are given to the same components as those of FIG. 1. All the controlling operations may be performed by a microcomputer. The specimen is coated by a given film on its one side, while it is free from coating of film on its other side, and is set between the measuring cells 1 and 1'.

Sometimes the measurement on the non-film side is to be performed, but the measurement of the film side is not to be performed or cannot be performed. This is, for example, when the specimen is one selected from the group of the sulfide stress cracking resistance materials and the embrittlement resistance materials, or when cell 1 is filled with a corrosive gas ($SO_2$ gas, steam), solid (soil) or non-electrolyte liquid (crude oil). In such cases measuring cell 1' is filled with a given alkaline solution (for example, a NaOH solution).

However, when judgement of the specimen's phenomenological behavior in an electrolyte is required, measuring cell 1 is filled with a given electrolyte (for example, NaCl solution) to perform the film side measurement. When a measurement concerning the non-film side is required or a temperature promoting test on the film side is performed, measuring cell 1' is filled with a given alkaline solution.

The given test conditions are input to a step controlling means (not shown here) which controls measuring steps as follows. When the specimen is not one for sulfide stress cracking resistance, or embrittlement resistance (a "NO" case) and a judgement of behavior in an electrolyte is required (a "YES" case), a measurement of the film side is arranged to be performed. In the case of a film side measurement (hereinafter referred to for brevity as an "anodic measurement"), the specimen plate W's electrode potential is measured by the spontaneous electrode potential detecting circuit 3 and stored in the spontaneous electrode potential storing circuit 18 so that data (9) can be obtained while plate W is potentiostatically electrolyzed at the spontaneous electrode potential with respect to the reference electrode. Potentiostat 2 maintains the proper state for the potentiostatic electrolysis described above.

During this potentiostatic electrolysis, cathodic and anodic pulses are applied between the specimen plate W and the counter-electrode C by the pulse potential generating circuit to pulse-polarize the specimen plate W. The cathodic and anodic pulse currents flowing between the specimen plate W and the counter-electrode C in response to the operation of the pulse polarization are stored in the storing circuit 8 and are fed to the comparing circuit 9 which judges whether or not the cathodic and anodic pulse-currents are the same. When they are substantially the same (a "YES" case), circuit 9 signals that no film-defects exist in specimen plate W (data (10)). Next, the cathodic and anodic pulse current values stored in circuit 8 are divided by cathodic and anodic pulse voltage values, by a division circuit 27 to detect the film's electric resistance (data (12)) and water permeating rate (data (13)). However, when circuit 9 indicates the cathodic and anodic pulse currents are judged not to be substantially the same (a "NO" case), the film detects (data (11)) are instead displayed.

The film's electric resistance and water permeating rate are detected as follows. When the pulse polarization is performed by step pulses $+E_p$ and $-E_p$ as shown in FIG. 12, the resulting pulse polarization current changes exhibit exponential decay portions as shown in FIG. 13. The time $\tau$ if takes the initial maximum value $i_{po}$, to decay by a factor of 0.3679 (1/e) is the current pulse time constant. The film resistance $R_f$ can be determined, according to the relationship of $R_f = E_p/i_p$, using of the asymptotic current value $i_p$ of time $5\tau$ (See FIG. 13). When the film resistance $R_f$ is obtained, the electrostatic capacity C of the film which is expressed by $C = \tau/R_f$ can be calculated. Also, since the attenuation curve of the pulse current in connection with the operation of the pulse polarization is expressed by $i = \text{EXP}[-(1/R_f C_f)t]$, $C_f$, $C_o$ are both obtained from this equation wherein $C_f$ is electric resistance of wet film and $C_o$ is electric resistance of dry film. The water permeating rate is obtained by the following expression, i.e., $A_p = 100 \log(C_f/C_o)/\log 80$ (%) wherein $A_p$ is water permeating factor.

After the operation of the pulse polarization is over, the specimen plate W is polarized by the potential scanning polarization method at a given rate with the linear potential sweep applying circuit 6. In case wherein no film-defects are found in the specimen plate W, a DC voltage is applied between the coated metallic plate W and the counter electrode C by the linear potential sweep applying circuit 6. The application voltage is varied with positive and negative grade. The electrolysis current flowing between the coated metallic plate W and the counter electrode C is input to a differential circuit 28 as a measured signal. However, a correction DC voltage varying in the same way as circuit 6's sweep output the application voltage is input to the differential circuit 28 to be used as in determining a current correction signal calculated by dividing this correction voltage by the electric resistance of the film. The difference signal between the measured signal and the correction signal is taken out by the differential circuit 28 so as to detect a very or infinitesimally small current-potential variation (data (14)). Namely, when substantially no film defects are found in the specimen W, the variation of the potential current (FIG. 15) which varies almost linearly is obtained in response to the linear potential sweep polarization (FIG. 14). However, when the very small current-potential variation (see FIG. 16) is isolated out, the corrosion current $i_{cor.}$ can be obtained from the following expression, $i_{cor.} = E_p^2/(\Delta E \cdot \Delta i \cdot i_p^2) \cdot 1/f_{exp.}\{f(\Delta E)\}$.

When film defects exist in the specimen plate W, the positive and negative log. i vs. E polarization curves are stored in the storing circuit 14 so that the curves can not only be displayed, but also utilized to detect the corrosion current and corrosion amount (data (16)) with the help of the circuit means 17. In addition, the peak detecting circuit 12 detects whether or not a peak exists in the cathodic polarization curve.

The peak detecting circuit 12 may be composed of a differentiation circuit. The $d(\log i)/d(E)$ variation which defines the cathodic polarization curve goes from its plus mode $\oplus$ to its minus mode $\ominus$ at a peak in such polarization curve such as A as shown in FIG. 7; thereafter if there is a local minimum such as B, it returns to the plus mode $\oplus$ again. Namely, the differential values become zero at both points A and B. Accordingly, when the differentiation circuit twice outputs a zero, the existence of a peak can be confirmed. When the potential and the current at the time corresponding to the first zero output are detected by the detecting circuit 15, the detected values give a "peak potential" and a "peak current", respectively. The polarization curve of the specimen plate W is measured regularly every time a predetermined time period elapses to determine the effect with time of contact with the corrosion liquid. The peak potential and peak current values of each polarization curve are stored at a storing circuit 29 to measure their variations with time (data (21)). The area related to the peak in the cathodic polarization curve ("peak area") is obtained with the circuit means 16.

As far as the cathodic polarization peak's variation with time is concerned, there are two types. According to one case, the whole cathodic polarization curve including its peak portion moves successively upward (i.e., the polarization current increases), e.g., ① to ② as can be seen in FIG. 18, with the given time period as a parameter. According to another case, only the peak portion of the cathodic polarization curve substantially moves upward, i.e., from ① to ③ as can be seen in FIG. 19.

In the whole curve upward case, the Tafel slope of the polarization curve ① is obtained by the use of the same technique as described earlier to decide a Tafel tangential line ①'. The area surrounded by that portion of the polarization curve above the Tafel tangential line ①' is obtained with the help of an integration circuit. The area is defined and obtained by the following expression, i.e., $$\int_{E1}^{EB} [f(E \, ①) - f(E \, ①')] \cdot dE,$$

wherein an integral starting $E_1$ point is a potential point where the measured value has been deviated from the tangential line, and an integral terminating point is a potential $E_B$ where the differentiation circuit of the peak detecting circuit 12 outputs the second zero output. However, the f(E ①) is a function representing the polarization curve, while the f(E ①') is a function representing the Tafel tangential line.

In the peak only upward case, the area defined and obtained by the following expression, i.e., $$\int_{E1}^{E2} [f(E \, ② \text{ or } E \, ③) - f(E \, ①)] \cdot dE,$$

wherein intersecting points of the polarization curve ① and the polarization curve ② or ③ are the integral starting point $E_1$ and the integral terminating point $E_2$, respectively.

Furthermore, when circuit 12 determines that a peak exists (a "YES" case) the electrode potential of the specimen plate W before testing by the polarization operation is compared by circuit 19 with that of the substrate metal, to determine whether the coated specimen plate's electrode potential is more cathodic or anodic than that of the substrate metal. With respect to the electrode potential of the substrate metal, as the substrate metal to be adopted for the specimen plate W is normally iron, the spontaneous electrode potential of iron is chosen as a reference. As a matter of fact, since the potential of iron differs depending upon such corrosion circumstances as PH and temperature, the electrode potential of bare iron under the conditions in which the specimen is to be tested is chosen as the reference.

If circuit 19 detects a cathodic mode (a "YES" case), the film defect portion is likely to suffer a pitting corrosion, see FIG. 20. Accordingly, the pitting corrosion (data (17)) is displayed. The corrosion amount or dimensions and its variation with time are taken into consideration to stereoscopically display the pitting corrosion state of the defected portion.

If circuit 19 detects an anodic mode (a "NO" case), the corrosion of the film defect portion is likely to spread over in the relatively lateral direction (crevice corrosion), see FIG. 21. Accordingly, the crevice corrosion (data (19)) is displayed, wherein the corrosion amount, the peak potential, the peak current and/or the peak area or the variation of features with time are taken into consideration, thereby to stereoscopically display the crevice corrosion state of the damaged section.

On the other hand, when the peak detector does not detect a peak (a "NO" case), the electrode potential of the untested specimen plate W is compared with the electrode potential of the substrate metal by the comparator circuit 19. In the case of the cathodic mode (a "YES" case), the defective film portion is likely to be corroded in the relatively lateral direction (crevice corrosion). In the case of the anodic mode (a "NO" case), the defective film portion is likely to be suffering from pitting corrosion. As is clear from the above description, for a given mode (cathodic, anodic) the relationship to the corrosion condition (pitting, crevice) can become reversed according to whether the cathodic polarization curve involves a peak or not.

In addition, when the information as to whether or not a metallic plating layer or a cathode corrosion preventing film exists between the film and the substrate metallic surface is intended to be obtained, the existence of the peak in the anodic polarization curve or the existence of the difference in the spontaneous electrode potential between the substrate metal and the coated metal are to be confirmed.

When a peak portion exists in the anodic polarization curve, the plating layer exists, wherein the polarization step requires the specimen plate W to be polarized by 500 mV in the anodic mode with respect to the level $E_{cor.}$ and to confirm whether or not the peak or the stage portion exists in this range.

The controlled defects stored in the film face of the specimen plate must be deep enough to exist even in the metal plating layer. Therefore, if for some reason there is no defect in the metal plating layer, the metal plating layer itself is judged to be the metallic substrate in the initial dipping stage of the specimen plate. Accordingly, if defect is deep enough to reach the substrate metal portion, first the plating layer can be confirmed to exist.

More specifically, a procedure shown in FIG. 11 is used for the detection purpose described above. The specimen steel plate W is polarized by approximately 100 mV in the cathodic mode with respect to the pontetial $E_{cor.}$ by the use of the linear potential sweep polarization method to obtain the cathodic polarization curve and is polarized by approximately 500 mV in the anodic mode with respect to the potential $E_{cor.}$ to obtain the anodic polarization curve.

Successively, the existence of the peak portion is detected from the cathodic polarization curve to obtain either an existence signal ⑨ or an absence signal ⑧. On the other hand, the existence of the peak portion is also detected from the anodic polarization curve to obtain either an existence signal ②, or absence signals ④ and ⑦. In addition, as is shown in FIG. 11, the electrode potential $E_{cor.}$ of the specimen steel plate W is compared with the electrode potential $E_{Fe}$ of the bare steel plate being under the same corrosion circumstance to obtain either the cathodic signal ① if $E_{cor.} < E_{Fe}$ or the anodic signal ⑥ if $E_{cor.} > E_{Fe}$.

In the case wherein the peak-existing signal ⑨ is obtained in the cathodic polarization curve, with the metal plating layer-absent signal ⑦ being simultaneously obtained due to the reason as described hereinabove, the corrosion form of crevice corrosion is then confirmed, subject to the condition that the anodic signal ⑥ indicating $E_{cor.} > E_{Fe}$ is obtained.

In the case where signal ② indicating that the metal-plating-layer exists is obtained, the corrosion form is confirmed to be the pitting corrosion when the cathodic signal ① indicating $E_{cor.} < E_{Fe}$ is obtained. Also, even when a cathodic corrosion-preventing-film existing signal ⑤, instead of that of the metallic plating layer, is obtained (a metal-plating-layer-absent-signal ④ as well as the cathodic signal ③ of the $E_{cor.} < E_{Fe}$ are both obtained), the corrosion form is confirmed to be the pitting corrosion. Furthermore, the $E_{cor.}$ of the specimen steel plate W becomes more cathodic than the $E_{Fe}$ signal despite the absence of the metal plating layer, since the corrosion preventing film will show the same functional characteristics as when the metal plating layer exists.

In the case where the peak-is-absent signal ⑧ is obtained in the cathodic polarization curve, with the metal-plating-layer-absent signal ⑦ being simultaneously obtained, when the anodic signal ⑥ showing $E_{cor.} > E_{Fe}$ is obtained, the corrosion form is found to be pitting corrosion. Furthermore, when the metal-plating-existing signal ② and the cathodic signal ① showing $E_{cor.} < E_{Fe}$ (the cathodic corrosion-preventing-film-existing-signal ⑤ is obtained) are both contained, the corrosion is confirmed to be the crevice corrosion.

According to the present invention, as indicated in FIG. 11(b) a model figure ⑩ which stereostatically displays the corrosion section of the film defect portion is drawn taking into consideration as data the corrosion volume ①, corrosion configuration (pitting corrosion or crevice corrosion) ⑫, peak area ⑬, and peak potential and peak current ⑭.

The corrosion volume ⑪ is a corrosion quantity ($W_g = i_{cor.} h_r / k$; where k is the electrochemical equivalent amount, hr is immersing time) divided by the specific gravity $\rho$ of the substrate metal. Accordingly, the following expression, i.e., $VOL._{cor.}(cm^3) = i_{cor.} h_r / k \cdot \rho$ is obtained. According to the present invention, the corrosion current $i_{cor.}$ can be obtained as previously described (see FIG. 7), and thus the corrosion volume $VOL._{cor.}$ can be obtained as long as the immersing time $h_r$ is measured, and the electrochemical equivalent amount k and the specific gravity of the substrate metal are both given as constant in advance.

Comparing FIGS. 20 and 21, since in the case of the pitting as in FIG. 20 there is substantially no rust width l spread laterally in the interface of the film and the metal surface from the film defect portion, only the surface area D of the film defect portion needs be taken into consideration to model the corrosion volume $VOL._{cor.}$ With respect to the surface area D, the corrosion current density $K_1(i_{cor.}/cm^2)$ of the bare substrate metal being in the same environmental condition as those for the specimen plate W can be measured in advance. Then $K_2$, the actual measurement of the corrosion current $i_{cor.}$, immediately after the dipping of the specimen plate W in the corrosion medium permits D to be estimated by the following relationship, i.e., $D = K_2 / K_1 \cdot (cm^2)$.

In the case of the crevice corrosion, as will be described below, the rust width becomes larger (see FIG. 21), the more the peak potential is cathodic, with the difference between the peak current value with respect to the peak potential and the current value represented by the Tafel tangential line (the substantial height of the peak) being correspondingly larger. Accordingly, when the relationship between respective variations of peak potential, current and/or the peak area with time and the rust width are appropriately taken into consideration, the accuracy of the model figure is improved. The crevice height denoted by H is generally in the range from several micrometers to several tens of micrometers, whereby it is not difficult to draw the model figure even if the exact values of the height described above are not obtained.

The peeled-off area $A_1$ of the film under the condition of the non-artificial prevention of spontaneous corrosion can be estimated from the peak potential $P_E$ and the peak area $P_A$ of the cathodic polarization curve. Namely, among $A_1$, $P_A$ and $P_E$, there can exist the following relationship, i.e., $A_1 = K'(P_A \times P_E)$, wherein K' is a constant related to the peak potential together with the peak area under the peeled-off area $A_1$.

The relationship between the existence of the peak in the cathodic polarization curve and the corrosion form, the peak potential, the peak current, the peak area, the variation of the peak area with time and the rust width will be clarified with reference to the following embodiments.

EMBODIMENT 1

The specimen plate used was, a steel plate (JIS. G, 3141: mold steel plate having the dimensions of 15×7×0.08 cm). The plate was coated to 200μ in film thickness with epoxide resin paint of the amine hardening type (Copon EA-9, tradename, marketed by Nippon Paint Co., Ltd.). Each coated steel plate W had a defect portion H on its coated side. A film defect area of approximately $1 \times 10^{-3} cm^2$ was confirmed in advance by the microscopic observation. As illustrated in FIG. 22, a silver-silver chloride reference electrode R and a platinum counter-electrode C were set adjacent to the defect portion H.

When the specimen steel plate W was polarized in the cathodic mode (50 mV per minute) at various times after immersing (50, 100, 200, 500, 1000 hours), a respective peak $P_1$, $P_2$, $P_3$, $P_4$, $P_5$ as shown in FIG. 23 appeared in the corresponding cathodic polarization curve. It was observed that the potential of each of the peaks $P_1$ to $P_5$ was likely to shift in the cathodic direction with increasing lapse of the immersing time.

On the other hand, as shown in FIG. 24, the rust width "a" of the defect portion H region and the film peeled-off width (a+2b), for each dipping time was measured according to the conventional method.

As shown in FIG. 25, it is found out that an approximately linear relationship exists between the variation of the rust width (x marks in the drawing) with time and the variation of the peak potential with time. Further an approximately linear relationship also exists between the variation of the peeled-off width (◯ marks in the drawing) with time and the variation of the peak potential with time.

Thus, when peaks appear in the cathodic polarization curve, by measuring the variation of the peak potential with time the rust width and the peeled-off width of the film defect portion can be estimated.

EMBODIMENT 2

The coating was an epoxide resin paint A. This was a spontaneous drying paint composed of two miscible liquid types of paste and a hardening agent; more specifically, it was composed of 40 percent PVC; 80 percent NV; and additives. The additives were a drip preventing agent+surface active agent, a rust preventing pigment+filter (body), and an epoxy resin. Alternatively the coating was a polyester resin paint B the same as paint A, except that polyester resin was employed in place of epoxy resin. The coating chosen was applied to a thickness of 500μ on steel plates each having the same standard as those used in the embodiment 1. Each coated steel plate was dipped in a 3% NaCl aqueous solution kept at 30° C. The plates were polarized under the cathodic polarization condition of 50 mV per minute for each immersing time (approximately 500 hours) to detect any peak potential which appeared in any of the polarization curves and to measure the rust width of the defect portion for each immersing time. The existence of a defective portion having an area of approximately $1 \times 10^{-3} cm^{-2}$ was confirmed in advance for each specimen by telescopic observation.

FIG. 26 shows the cathodic polarization curves of the specimen steel plates A and B during 500 hours' immersing operation. As apparent from FIG. 26, peaks were seen in the A specimen steel plate, but no peak appeared in respect to the B specimen plate. Further tests confirmed that for B specimen plate peaks did not appear until 1,500 hours' immersing time.

According to the observation of the rust width of each of the specimen steel plates A and B during 500 hours' immersing operation, only the rust width in the specimen steel plate A was likely to develop into the pitting.

From the result as described above, in the A specimen steel plate the rust width is likely to spread in the lateral direction soon after the peak appears in the cathodic polarization curve.

Referring now to FIG. 27, the aging variation of the peak potential in each of the polarization curves of the specimen steel plates A and B shows the same inclination as that of the aging variation of the rust width (see FIG. 28), whereby the interrelation therebetween can be understood.

EMBODIMENT 3

The specimens were steel pipes C and D. Each had a 100 mm inner diameter and was 5 mm thick. Pipe D was under coated by a zinc-phosphate film prior to coating of with paint, while the steel pipe C was not undercoated. Each was coated, to a thickness of several millimeters, with polyethylene paint and installed in soil lying approximately 1 m in depth below a road surface and having a relative moisture content of 10 percent.

The location where the damage was considered to be effected during the installing operation was polarized in the cathodic polarization method with the help of the same method as described in the embodiment 1.

FIG. 29 shows the cathodic polarization curves after 100 hours' of immersing specimen steel pipes C and D. When the corrosion current is obtained from the cathodic polarization curve for each immersing time by the use of an ordinal extrapolation method, the variation of the corrosion current with time can be correlated with respect to the immersing time as shown in FIG. 30.

For pipes C and D rust is likely to spread relatively laterally or in a narrow splitting mode from the film defect portion. Under the conditions above, it can be estimating from FIG. 30 that the rust effected in pipe C spreads about ten times as fast as the rust effected in pipe D spreads. This phenomenological feature corresponds to the difference in the current value of the peak portions in each of the polarization curves shown in FIG. 29. Accordingly, a corrosion estimation equivalent to that accomplished by the use of the corrosion current correlation as described above can be accomplished by reading the peak currents of the polarization curves. In fact, as can be seen from FIGS. 30, 31 and 32, the trend or feature of FIG. 31's aging variation in the peak current of the polarization curve is approximately the same as the trend of the aging variation (see FIG. 32) of the rust width and the trend of the aging variation (see FIG. 30) of the corrosion current.

In general, if a quite cathodic peak potential appears in the initial stage of the immersing operation, namely, when the rust spreads extremely in the initial immersing stage, the peak potential does not easily shift towards highly cathodic values as immersing time increases; this is being different from embodiment 2 where the peak potential gradually becomes more cathodic with time. Accordingly, in such a case as described above, since the peak current almost relatively corresponds to the corrosion current as described previously, the peak current can serve as a substitute for judging the variation of the rust width. Thus, the form or configuration and the expanse of the rust can be also estimated from the peak electric current value and its variation with time.

EMBODIMENT 4

The coating was epoxy resin paint of the type sold for coloring zinc-plated sheet metal. The paint applied to have a paint-film thickness of approximately 50 μ and dried at 170° C. for 10 minutes. it was used to coat a commercially available fused zinc-plated steel plate E, size $15 \times 7 \times 0.03$ cm. Also a second plate F of the same kind which had been finished by the use of the normal chromic acid treatment was coated by the paint. A third steel plate F' which was treated by ordinarily electroplated zinc finish was also coated by the paint. With respect to the specimen plates E, F and F', their cathodic polarization curves were respectively obtained, with the immersing time being chosen as the parameter for each of the dipping operations carried out in the same manner as in the embodiment 2. FIG. 33 shows each of the cathodic polarization curves after 20 hours' immersing operation. As can be seen in FIG. 33, the specimen plates E, F and F' show the spontaneous electrode potential of approximately −1 volt, respectively. With respect to the specimen paltes F and F', the peak or stage appears in each polarization curve. But no peak appears in the polarization curve of the specimen plate E and the rising feature of the polarization curve is larger than those of the specimen plates F and F'.

For the same specimens a visual corrosion evaluation was also performed and the results obtained from the respective variations of the rust width with respect to time is shown in FIG. 34. With respect to the specimen plates F and F', the increase in the rust width with time is not remarkable, whereas with respect to the specimen plate E, there is significant increase in the rust width with time. Namely, in the specimen plates F and F', the development of pitting corrosion in the film defect portion was confirmed.

Accordingly, from the above results, an estimation can be made as follows. In the fused zinc-plated steel plate, the pitting corrosion behavior is shown when the peak and the stage portion are effected in the cathodic polarization curve. When the cathodic polarization curve rises without peaks and stage portion, the rust width tends to show the increasing behavior. Namely, as far as the specimen plate E is concerned, only the plated layer is to be corroded and the steel plate of the substrate is protected from the corrosion. Accordingly, the quantity of electricity of $i_{cor.}$ of the E corresponds to the variation in the rust width. On the other hand, in the specimen plates F and F', the corrosion inhibiting reaction in the substrate steel plate subject to the plating is not effective. It is needless to say that the aging variation of the depth of the pitting corrosion of the specimen plates F and F' can be substantially estimated from the aging variation (see FIG. 35) of the peak potential of the polarization curve or $i_{cor.}$. It is to be noted here that the results just described above are opposite to the corrosion behavior estimated from the cathodic polarization curve of the specimen plate of embodiment 2 which was not zinc-plated.

EMBODIMENT 5

With respect to specimen plates G and H, the cathodic polarization curves were respectively obtained, with the immersing time being chosen as the parameter for each of the immersing operations carried out in the same manner as in the embodiment 2. Commercially available paint G" (35% PVC, 60% NV, epoxy-acrylic resin, non rust-preventing pigment) and H" (commercially available paint G" further including rust-preventing pigment) were coated, to the thickness of appropriate 15μ, on the fused zinc plated steel plate F which was used in the embodiment 4, thereby to prepare the specimen plates H and G. FIG. 36(a) shows the cathodic polarization curve and FIG. 36(b) the anodic polarization curve for specimen plates G and H after 250 hours' immersing operation. As can be seen from the cathodic polarization curve of FIG. 36(a), a substantial peak appears, whereby it can be estimated that the rust width is likely to be spread in the lateral direction or in the splitting mode. However, a rise occurs after the peak in the polarization curve of the specimen plate G, whereas the polarization curve of the specimen plate H becomes approximately flat after the peak.

Concerning rust width aging variation (see FIG. 37) plate G's rust width is constantly larger than plate H's, and this pattern is repeated in the peak potential aging variation (see FIG. 38) where G's peak potential consistently exceeds H's. However, comparing the cathode polarization curve FIG. 36(a) of plate G with E of FIG. 33 for the specimen plate E of the embodiment 4, two current values show approximately the same variation. However the aging variation of the rust width FIGS. 37 and 34 is considerably less for plate G than for E. Accordingly, as far as the specimen plate of the present embodiment is concerned, the behavior of the pitting corrosion can be estimated to overcome the tendency of the increase in the rust width as the peak and the stage portion in the cathodic polarization curve appears.

Therefore, the overall corrosion evaluation can be performed by the confirmation of the existence of the peak in the cathodic polarization curve, and by the use of the potential and current values of the peak. For example, the corrosion behavior of the specimen plate G can be judged to show the corrosion behavior of the specimen plates E and F of the embodiment 4 from the existence of the peak, the peak potential and peak current of the polarization curve (G of FIG. 36(a)) of the specimen plate G.

FIG. 36(b) shows the anodic polarization curves of the specimen plates G and H after 250 hours' immersing operation. In the initial stage of the polarization operation, peak or knee portion is seen in the anodic polarization curve, since the dissolving reaction of the zinc-plated film is a rate-determining step or a rate-controlling step in the initial stage of the polarization operation, but the dissolving reaction is restrained from occurring as the polarization potential becomes more anodic and the polarization current does not follow the increase of the potential. Thereafter, the polarization current tends to increase following the increase of the potential, since the dissolving reaction of the substrate metal of the iron may exist. This phenomenon is unique when the metal plating lever exists between the film and the substrate metal. Accordingly, the detection of the peak in the anodic polarization curve makes it possible to detect the existence of the metal plating layer.

EMBODIMENT 6

The specimen plate H of the embodiment 5 was prepared and also a specimen plate I (the same point was coated on steel plate I which is higher in respect to surface spangle than the zinc-plated steel plate of the specimen plate H). Cathodic polarization curves were measured at the immersing initial stage (0.5 hour) and for each immersing time in the same manner as described in the embodiment 2. The result is shown in FIG. 39 (specimen H) and FIG. 40 (specimen I). Referring to FIG. 39, an interrelation can be observed between the aging variation of the peak area of each polarization curve (the area surrounded by the initial immersion (0.5 hour) polarization curve and each later polarization curve) and the aging variation (see FIG. 37) of the rust width. Accordingly, the rust width can be estimated from the area of the cathodic polarization curve's peak portion. An interrelation may also be shown between the aging variation of the area in respect to the peak portion of FIG. 40 and the aging variation of the rust width. However, specimen H's increase rate relating to the area of the peak portion shown in FIG. 39 is larger than specimen I's increase rate relating to the area of the peak portion of FIG. 40, indicating specimen I has a feature opposite to the variation of specimen H's rust width. Namely, the specimen H of embodiment 6's FIG. 39 shows a feature similar to the specimen H of the embodiment 4. But specimen I of embodiment 6's FIG. 40 shows a feature similar to specimen G of embodiment 5. Accordingly, from the area and/or the aging variation of the peak portion, the corrosion behavior, especially the rust width and the variation thereof can be estimated.

FIG. 41 shows the anodic polarization curve of the specimen plate I after 0.5 hours' immersing operation. Since the specimen plate I is coated by a metal plated layer, a peak appears in the anodic polarization curve as can be seen in FIG. 36(b).

The above embodiments show one example of the corrosion evaluation testing methods according to the present invention.

Generally, in the study of clearance corrosion or its practical evaluation, the corrosion behavior caused by a small clearance between metal and metal or metal and nonmetal has been considered as a serious problem as shown in FIG. 42, wherein a preferable experimental object is a specimen plate whose contact area ⓐ' between the face of a metal ① and the liquid ② is larger than the clearance portion ⓑ'. However, as far as the case of the coated metallic material (hereinafter the metallic material is specifically assumed to be steel plate) is concerned, when a very small defect exists in the film (see FIG. 43), the width W or the length of the defect is small. Actually, the liquid ② is only in contact with the metallic portion directly below the defective width W, even if metal ① is in contact with the liquid ②. Due to a decrease in film ③'s electric resistance caused by liquid absorbed in film ③, liquid penetrates into the interface of film ③ and the metal ① by water permeation. When the metal ① is polarized, the current flows in film ③, but generally this current is considerably smaller than the current flowing in defect portion W. Accordingly, the area through which the current can flow easily to the metal during cathodic polarization is smaller in FIG. 43 even if respective cases of FIG. 42 and FIG. 43 are both polarized in the cathodic mode under the same condition.

When the rust (represented by black in the figures) spreads from the defect portion and reaches to a certain depth as shown in FIG. 43. However, even if the H of FIG. 43, including the clearance width is the same in value as the H of FIG. 42, the metallic face ⓐ corresponding to the defect width W is much smaller than the portion of the metal face ⓑ where the rust has spread. But in FIG. 42, when the metal face ⓐ' in contact with the liquid (except for the clearance portion) is much larger than the metal face ⓑ' of the clearance portion. Thus, the phenomenological behavior inside the clearance ⓒ' of FIG. 42 is substantially subjected to the reaction relating to the metal face ⓐ' and is far from being independently effected.

On the other hand, in the case of FIG. 43, the metal face ⓐ is smaller in area than the metal face ⓑ and thus the reaction inside the clearance ⓑ becomes distinguishable from the reaction of the metal face ⓐ. As a result, with respect to oxygen amount, ion concentration or the variational amount of the liquid components due to polarization, there regional differences will exist between portion ⓐ and portion ⓑ, or between the liquid ② and portions ⓐ, ⓑ. Thus, the behavior inside the portion ⓑ may have for example, a peak on its cathodic polarization curve. However, when the rust width ⓓ and the peeled-off width ⓔ are small relative to such deep corrosion as shown in the dotted line ⓒ in FIG. 43, the clearance or crevice ⓑ portion is also small. Hence, the behavior inside approximately the dotted lines is apparently measured overall, so that its behavior becomes similar to a normal cathodic polarization curve having no peak at all.

As is clear from the above description, the peak-causing mechanism is due to the phenomenon of the clearance corrosion or crevice corrosion under the film. From this, the corrosion configuration of the defect portion can be estimated from the existence of a peak, whereby an extremely advantageous corrosion evaluation testing method can be provided according to the present invention.

Respective values of the peak potential and current which both appear in the cathodic polarization curve are likely to increase (the potential is increased in the cathodic mode) in accordance with a rise in temperature. It may be preferable to perform the preliminary corrosion evaluation measurements at temperatures ranging from 15° to 40° C. corresponding to natural environmental conditions. But it is also very informative to observe the variation of the peak potential as a function of temperature variation to learn the temperature dependency of the corrosion behavior.

Furthermore, since polarization speed influences the polarization behavior of the specimen plate, it is preferable to select the proper conditions. Generally a polarization speed of 10 to 500 mV per minute is selected. In this range, not only the peak potential varies towards the anodic mode, but also the peak current is likely to increase with an increase in polarization speed.

Also, conventionally polarization curves are obtained by continuously recording the relationship between the current and potential. However, the present invention permits storing the polarization current values at selected, spaced potential values and combining the stored values to give polarization curves correlating the relationships of i vs. E and log i vs. E. In this case, to obtain the peak current or the peak potential, for example, the current variation from which the polarization curves are established is differentiated with the help of a differentiation circuit thereby to obtain the current value or the potential value when the current's slope becomes zero.

Now we will turn our attention from film side measurements to non-film side measurements. Referring to FIG. 10, when the specimen is one prepared for tests relating to hydrogen cracking resistance or sulfidation attack resistance (a "YES" case), or a measured behavior judgement of the specimen in electrolyte is unnecessary (a "NO" case), the non-film side (reverse side of the specimen plate) is brought into contact with an alkaline test liquid and potentiostatically electrolyzed. First, define the corrosion condition. Then the potential of the non-film side is set to zero with respect to the non-film side reference electrode and held at this initial potential with the help of potentiostat 2'. Whereby atomic hydrogen produced on the film face side and diffusing through the steel to the non-film face side is ionized at the interface between the non-film face and the alkaline liquid, causing a flow of ionized current between the specimen plate W and the counter-electrode C'. This is measured by an electrolysis current measuring apparatus 7' and the variation is stored at the storing circuit 21 and then further displayed (data (1)).

EMBODIMENT 7

As the specimen plate W, a polished steel plate of 0.8 mm in thickness was used, which was treated with a zinc-phosphate formation film. One face of the plate was coated to $35\mu$ in film thickness, with paint substantially composed of melamine-alkyd resin mixed with a 1% by weight rust preventing agent. The coating was dried at 140° C. for 30 minutes. A 3% NaCl solution maintained at 50° C. was put into left-hand measuring cell 1. The right-hand measuring cell 1' was filled with one Normal NaOH Solution maintained at 15° C. The specimen palte W was set at an electrode potential of zero with respect to the right hand non-film side reference electrode, being potentiostatically electrolyzed for 25 hours. The variation in the electrolysis current flowing between the counter-electrode C' and the specimen W is shown by dotted line A in FIG. 44.

The dependency of current relating to steel substrate with immersion period as shown in FIG. 44 can be considered as follows:

Three peaks P1, P2, P3 are made with the dotted line A in FIG. 44. Note that a certain time $t_c$ the rise for peak P3 begins.

Since the first peak P1 is caused by the variation in the electrolysis current in the initial contact stage of the specimen substrate W with the liquid, the first peak P1 is effected by the corrosion-corrosion preventing reaction between the steel substrate on the non-film coated face and the NaOH solution, judging from the turn of a series of the reaction steps relating to the specimen plate W. More specifically, the first peak P1 is effected after approximately 0.1 hour from immersion, peak current being approximately 10µ A, even when both liquids are maintained at 50° C. so that there is no temperature gradient between the two sides of the specimen plate W. Therefore, the generating time is too soon and the current described above is excessive for hydrogen to be dissolved due to corrosion of the steel plate under the film and then penetrate to the non-coated face.

Actually, since the current value depends upon the surface condition on the non-coated face, the variation relating to electrolysis at the spontaneous electrode potential is measured, instead of potentiostatic electrolysis. The result obtained shows that a locally minimum variation in respect to the electrode potential appears near the first peak P1, wherein the corrosion-corrosion preventing reaction on the non-coated face must be effected. The time dependent electrolysis current due to the reaction of the non-coated face with NaOH solution is shown by a curve B in FIG. 44.

Accordingly, curve B having first peak P1 when added to later currents caused by the discharge of the atomic hydrogen in the steel substrate out of the non-coated face and its successive reaction of ionization, i.e., $H = H^+ + e^-$, contributes to the final form of curve A, particularly, peak P1.

With respect to the second peak P2, when the NaCl solution first reaches the metal face under the film to cause the corrosion reaction, i.e., $H^+ + e^- = H$, atomic hydrogen caused by the cathodic reaction penetrates into the metal face and drives out atomic hydrogen dissolved in the steel substrate at the non-coated face, causing curve C. That is curve C has P2 corresponding to an electrolysis current arising from the hydrogen dissolved originally in the steel which is caused to flow out the non-film side when the corrosive liquid reaches under the film after the immersing operation.

The third peak P3 is caused when the variation in electrolysis current as denoted by the curve C is over. Peak P3 belongs a curve D representing the atomic hydrogen caused by the corrosion reaction finally permeating through the steel.

The above description is confirmed by the following experimental facts. The second peak P2 hardly appears if a saturated NaCl solution is introduced so as to lower the diffusional rate of solution towards the film. Furthermore, the rising point $t_c$ of the third peak P3 corresponds to the time when rust, such as visually red dust, appears, indicating the atomic hydrogen liberating corrosion is well under way.

As is evident from the description concerning FIG. 44, since the curve A represents the over-all variation of the electrolysis current caused by superimposing electrolysis currents B, C, D of FIG. 44, the corrosion resistance of the coated metallic plate, i.e., the corrosion under the film, the hydrogen cracking inside the metal, stress corrosion, etc. can be properly estimated and evaluated by simply analyzing the over-all curve A.

EMBODIMENT 8

As the specimen, a polished steel plate was used. The plate was first coated by the zinc-phosphate-film treatment and then, was further coated on one face with the paint of the three time coats and three time bakes painting type. For a second coat of paint, two types, i.e., a corrosion resistant paint A and an easily corrodable paint B were used on separate specimens, named respectively A and B. The aging variation of the electrolysis current was measured under the same testing conditions as described in the embodiment 7. The result is shown in FIG. 45.

According to the graph shown in FIG. 45, the variation in the electrolysis current with respect to the immersing time for both specimens A and B is the same until the time $t_c$ which begins the rise of specimen B's third peak P3, i.e., up to approximately 15 hours after the start of the measurement. However, thereafter, it requires an additional 17 to 18 hours to reach the time when the rise of corrosion resistant specimen A's peak P3 begins, namely point $t_c$ of specimen A's curve. Also, the slope towards third peak P3 of specimen A is not as steep as the slope of specimen B's third peak P3.

With respect to the fact that the second peak P2 was the same for both specimens A and B, this suggests there was no significant difference in the diffusional rate of water into the respective films between the specimen A and the specimen B. Furthermore, it is estimated that the driving force for driving out the dissolved hydrogen caused by the effects combined by the corrosion liquid permeating rate on the coated face side and its accompanying corrosion reaction as well as the steel structure through which the melted hydrogen permeates are the same for both cases. The above-described estimations are confirmed as follows: (i) The second peak appeared even when the diffusion of solution into the film was suppressed in a moderate way. On the other hand, when saturated NaCl solution was employed, the dehydrating step worked and it was difficult to confirm the occurrence of the second peak. Due to the phenomenological features as described above, it may be concluded that the second peak is caused whenever water molecules, even in small amounts, reach the metal under the film. (ii) When the steel plate on the paint-film forming side is electropolished, the surface distortion layer caused by surface working is removed and the quantity of current caused after the first peak P1 is extremely large. (iii) The relationship between the logarithmic value (log t) of the time t when the second peak P2 is effected and the temperature of the immersing corrosive liquid on the coated face side becomes linear. The slope of the above relationship becomes the same as the slope which can be obtained when the logarithmic values (log D) of the diffusion coefficient D of the immersing liquid in the film and the measuring temperatures employed are correlated.

Accordingly, the diffusional characteristics of the immersing liquid can be judged by the time t relating to the second peak P2. After having been brought into contact with the film side, the corrosion liquid is diffused into the paint film, and the atomic hydrogen produced through corrosion on the metal surface is diffused in the metal to reach the non-paint film coated. Upon the quantitative calculation of the characteristic features described above, the time t relating to the second peak is considered as time required for the atomic hydrogen to reach the non-coated surface. Thus, the relation $t_p{}^2 = l_f{}^2/D_f + l_H{}^2/D_H$ is established, wherein $l_f$ is the film thickness, $l_H$ is the metallic plate thickness, $D_f$ is a diffusion coefficient of the liquid in the film and $D_H$ is a diffusion coefficient of the hydrogen in the metal. Such being the case, if the value of $D_H$ is given, the value of the diffusion coefficient $D_f$ can be determined by the following relationship, i.e., $D_f = (t_p{}^2 - l_H{}^2/D_H)/l_f{}^2$.

Furthermore, the esistence of the second peak P2 depends on the paint film type employed. More specifically, in the case of dry type paint, the amount of the water near the steel face under the film is relatively larger than for paint of the baking type. However, as far as the use of the dry type is concerned, while corrosion reaction always proceeds, the reactivity of the dry type with the water which newly reaches to the steel face through the film is not so high.

On the contrary, the reactivity of the baking type with the water newly reaching the steel face through the film is quite high. Accordingly, the occurrence of the second peak P2 is confirmed in the case wherein the baking type paint is employed, while it is not confirmed in the case wherein the dry type is employed. Also, the second peak was not confirmed in the case wherein the paints of the aging deterioration type are employed as the film.

Recall from FIG. 45 that the rising point $t_c$ of the third peak P3 is rendered earlier in the use of the specimen B (easily corrodable paint) than in use of the specimen A (corrosion resistant paint). This fact shows that the corrosion can be considered to start relatively earlier for the specimen B, since the time point denoted by $t_c$ almost coincides with the intersection between the curve C shown in FIG. 44 (the variation of the ionization current which is caused by the discharging or flowing out phenomenon of the hydrogen dissolved in the steel) and the curve D (the variation of the ionization current which is caused by the discharging or flowing out phenomenon of the hydrogen newly diffused into the steel through the corrosion reaction). It is confirmed that this fact coincides with the characteristics of the paint used and the production of the red rust.

Particularly, in high tensile steel which suffers corrosion reaction due to hydrogen, such as hydrogen cracking or the like, the relationship, i.e., $T = C \cdot t_c - k$ (hrs.) has already been confirmed to be established between the breaking time or the time required for the breaking T and the rising time $t_c$ of the third peak P3. The constant C is related to the characteristics of the steel material itself (for example, as the tensile strength is larger, it becomes smaller) and the grade or magnitude of the tensile stress applied upon the specimen plate W (as the stress increases, C becomes smaller). The constant k is related to the thickness of the steel material employed (as the material's thickness increases, k becomes larger).

The steeper rising feature of the third peak P3 in respect to the specimen B shows the faster generating rate of the melted hydrogen. This means the relatively faster corrosion reaction. Also, since the area (which specifies the quantity of electricity $Q_3$) of the third peak P3 shows the resolution amount of the atomic hydrogen in the steel, which is caused through the corrosion reaction on the film side, the area described above relates to the corrosion amount of the coated face. More specifically, with respect to the relation between the area (the resolution amount of the atomic hydrogen in the steel) and the corrosion amount as described above, the relation is further confirmed from the results of FIG. 46 showing the relationship between the length $F_l$ of visually observed filiform rust and the amount of the hydrogen melted in the coated steel plate which is calculated from the quantity of electricity of the third peak P3, and from the results of FIG. 47 showing the relationship between the visually observed corrosion width $l_{cor.}$ according to the salt spray test and the amount of the hydrogen melted in the coated steel plate, and from the results of FIG. 48 showing the relationship between the pitting corrosion depth HP obtained by the microscopic observation and the amount of the hydrogen dissolved in the coated steel plate.

Accordingly, a relation between the quantity of electricity $Q_3$ specific to the third peak and the crevice-rust width $l_{cor.}$ in the case of the lateral corrosion is given as follows:

$$l_{cor.} = a_1 \cdot Q_3 - K_1$$

wherein $a_1$ is a constant specified by the corrosion occurring environmental conditions, $K_1$ is a constant specified by the corrosion occurring environmental conditions together with the pH-value of a water soluble material contained in the coated film.

Also, a relation between the quantity of electricity $Q_3$ of the thrid peak and the filiform rust length Fl on the coated film side can be given as follows:

$$Fl = a_2 \cdot Q_3$$

wherein $a_1$ is the same as described hereinabove, and $a_2$ is a constant specified by the corrosion occurring environmental conditions together with the coated film.

Furthermore, the quantity of electricity $Q_3$ of the third peak P3 is proportional to the spontaneous electrode potential (corrosion potential) $E_{cor.}$ of the specimen plate W and the relation between them can be given as follows:

$$E_{cor.} = -a_3 \cdot Q_3 + Eo \text{ (volt)}$$

wherein $a_3$ and Eo are constants each being specified to the corrosion occurring environmental conditions. For example, as the pH-value of the water soluble material inside the film is smaller, the value of the constant $a_3$ becomes larger and the value of the constant Eo becomes more cathodic. On the other hand, as the pH-value becomes higher, the value of $a_3$ becomes closer to zero.

$Q_3$ is related to the pH-value and can be correlated as follows:

$$Q_3 = k \cdot (SpH) - 8$$

wherein k is a constant related to the soluble material in the film, the corrosion occurring environmental conditions, the film diffusion coefficient specific to the coated film, etc. and (SpH) is the pH-value prevailing over the metal surface under the coated film.

Moreover, when, for example, zinc-plated layer or zinc-rich undercoating film exists, Eo shows extremely cathodic (−) in potential. The value of $Q_3$ is generally larger, too. When the zinc-plated layer, etc. exists between the film and the metal surface, the corrosion preventing performance is larger. Therefore, assume that the corrosion preventing performance is designated by $A_f$, the corrosion preventing performance can be given as follows:

$$A_f = |E_{cor.}| + Q_3$$

wherein $E_{cor.}$ is normally more cathodic (−) in potential when compared with that of the spontaneous electrode potential of the steel under the same corrosion occurring environmental conditions. Thus, the corrosion preventing performance or capability can be estimated from the corrosion potential $E_{cor}$ and the quantity of electricity $Q_3$ of the third peak.

It is to be noted here that some steel plates do not show such third peak P3 as shown in FIGS. 44 and 45. For example, as for the specimen steel plate, the polished steel plate was first coated or treated by the zinc-phosphate-film treatment and then, was further coated on its one side face with a styrene-butadiene block terpolymer paint with tannic acid of 1% by weight as a rust preventing agent being mixed therein. The coated face side was in contact with 3% NaCl solution of 50° C., while the non-coated face side was in contact with one normal solution of NaOH of 15° C. The specimen plate was immersed for 20 hours so as to measure the electrolysis current (see FIG. 49). In this case, when the visual observation is further taken into account, one can understand the reason why the third peak P3 is not seen is derived from the phenomenological feature that the red rust was not effected, but alkaline blisters without rust were spotted among the black rusts.

The relationship between the blister on the film side and the quantity of electricity $Q_3$ of the third peak can be given as follows:

$$B = 1/(b \cdot Q_3) \times 100 \; (\%)$$

wherein b is a constant specified by the corrosion occurring environmental conditions and B(%) is the proportion of the blister area per the measuring area of the specimen plate W.

Needless to say, as apparent from the description with reference to FIG. 44, it is to be noted here again that the curve A shown in FIG. 44 is the overall curve superimposedly composed of the curves B, C, D. Therefore, for example, the second peak P2 is difficult to be effected when the rising step of the curve D is relatively earlier than those of the rest curves. Thus, various variational features relating to the curve A are brought about by the combined effects of the characteristics of the coated steel plate and the corrosion liquid.

Accordingly, the observation of the second and third peaks is to be performed for the corrosion detecting purpose.

As for the second peak detecting circuit, the same differentiation circuit may be used as is used in detection of the peak or the stage portion of the above described cathodic or anodic polarization curve. Referring back to FIG. 10, when the second peak exists (in the case of YES), the film of the specimen can be judged as the baking type film (data (2)). When no second peak exists (in the case of NO), the film of the specimen plate can be judged as the dry type or the aging deterioration film (data (3)).

The third peak detecting circuit 23 may be also composed of the same means as can be found in the second peak detecting circuit 22.

When the third peak exists (in the case of YES), the peak area is measured, thereby to detect the hydrogen amount (data (4)) which concerns the corrosion reaction to be effected on the film side. Then, the rising slope of the peak is measured thereby to detect the diffusional rate of hydrogen (data (5)). In addition, the rising time point $t_c$ of the third peak is detected thereby to predict the breaking time (data (6)) of the specimen plate W. On the other hand, when no third peak exists, no rising portion of the third peak exists. Thus, the superior corrosion resistance (data (8)) is displayed.

Referring now to FIG. 50, there is shown a block diagram of an apparatus which can detect the existence of the second peak P2 from the electrolysis current variation, the area (the quantity of electricity) of the second peak P2, the time of the second peak (the second peak generating time), the existence of the third peak P3, the rising time $t_c$ relating to the third peak P3, and the time (the generating time) and area (the quantity of electricity) of the third peak P3.

When the typical electrolysis current variation to be indicated by the dotting curve A of FIG. 44 is input into the apparatus as shown in FIG. 50 through the electrolysis current detecting means 7' shown in FIG. 50 (corresponding to the means of FIG. 1, having the same numeral number), the aging time up to the local maximum, minimum point P1, X, P2, $t_c$ and P3 of the curve A, namely, time up to the first peak point or apex, time up to the second peak rising point and time up to the second peak point, time up to the third peak rising point and time up to the third peak point are respectively detected. Furthermore, area of the second peak P2 and area of the third peak P3 (area after the third peak rising point) are detected. Each of the signals is sent to the processor unit 20 shown in FIG. 1.

More specifically, upon the measurement relating to the non-film side, the electrolysis current signal is input into the differentiation circuit 401 and to a differential circuit 402.

A signal which was input to the differentiation circuit 401 is differentiated here. When the signal at the local maximum point P1 of the curve A is input into the differentiation circuit 401, the output naturally becomes zero. A zero voltage detecting circuit 403 is further connected to the output side of the differentiation circuit 401 to detect the existence of the inflection point. The inflection existence signal is once amplified by the amplifier 404 and is input into a contact switching circuit 405. Thus, the contact switching circuit 405 is changed over from the contact A1 of the measurement start of a multistage contact L1 to the contact A2.

An oscillator 406 is connected to respective contacts A1 to A5. The oscillator 406 transmits a pulse signal to a time-counting circuit 407 by a start signal (measuring start), thereby to permit the time-counting circuit 407 to count the number of the pulses and to store or display the aging time. The counted-up number of the pulses is transmitted to a time-counting circuit 408 to add and count the counted-up number up to the following local minimum point X. Since the contacts A1 to A5 are arranged to be changed over among the respective local minimum and maximum points P1, X, P2, $t_c$, the aging time up to each of the inflection points described above is stored or displayed in each of time-counting circuit 407 to 411.

As described previously, in some specimen plates, the second peak P2 may not appear. In this case, it is to be noted here that respective outputs of the time-counting circuit 408 and 409 concerning the second peak P2 are adopted for or become the time of $t_c$ and the time of P3.

On the other hand, the electrolysis current signal which was input to the differential circuit 402 includes the current portion (shown by the curve B in FIG. 44) which is caused by the corrosion preventing and corroding operations between NaOH and the reverse face of the steel plate and does not directly concern the present corrosion evaluation purpose. Therefore, to subtract the current portion described above, the variation in the curve B is output from a storing circuit 412 which stores the variation of the curve B in advance by a starting signal (measurement start), thereby to input the variation of the curve B to the differential circuit 402. Accordingly, the output signal from the differential circuit 402 represents the variation provided through a subtraction operation of the curve B from the variation of the curve A, i.e., the combined variation to be effected by the curve C and curve D. The compensated output is then input to an integration circuit 413. The output side of the integration circuit 413 is connected to a second peak (P2) area displaying circuit 414 and a third peak (P3) area displaying 415 through a multistage contact L2. The multistage contact L2 per se is controlled by the contact switching circuit 405 described above. Since the second peak (P2) area displaying circuit 414 is connected to respective contacts $A_2$ to $A_4$, the integration value of the curve C from the inflection point X to the inflection point $t_c$ is displayed. Since the third peak (P3) area displaying circuit 415 is connected to respective contacts $A_4$ to $A_5$, the integral value of the curve D after the inflection point $t_c$ is displayed. These values of the areas each being specified by the quantity of electricity are sent to the processor unit 20 to perform the above-described purpose.

As described in the foregoing, according to the present invention, the quantitative or qualitative measurement values which are effective to estimate the corrosion of the specimen plate W can be obtained from the measurements concerning either each or both of the film side (surface side) and the non-film side (reverse side) of the specimen plate W. The user or the operator can select desired measured values optionally from the above-described measured values. With respect to the coating metallic material being in practical use, the corrosion can be evaluated, with the corrosion occurring environmental conditions, film characteristics (features of the film including the film thickness, the details concerning pre-treating operation), tensile stress and metallic characteristics (metal type, thickness, etc.) being simultaneously taken into account. In the apparatus of the present invention, each of the function of, for example, the collecting, recording, calculating means, i.e., the processor unit, can be arranged to be performed by a plurality of independents means. Furthermore, with respect to a step controlling means, it is not necessarily composed of means for centrally controlling each of steps.

Although the present invention has been fully described by way of example with reference to the accompanying drawings, it is to be noted here that various changes and modifications are apparent to those skilled in the art. Therefore, unless otherwise such changes and modifications depart from the scope of the present invention, they should be construed as included therein.

What is claimed is:

1. A method of testing coated metallic material for corrosion, comprising the steps of:
    (a) providing a metallic specimen plate having a film face coated by a film of paint and bringing the film face in contact with a corrosive test medium;
    (b) detecting the plate's spontaneous electrode potential with respect to the corrosive medium and potentiostatically electrolyzing said film face at said spontaneous electrode potential;
    (c) selectively pulse polarizing said film face by cathodic-anodic voltage and computing the existence or non-existence of a film defect from the polarizing voltage and detected induced polarization current;
    (d) selectively sweep polarizing said film face by a linear positive and negative potential sweep to induce a sweep polarization current;
    (e) responding to the computation of non-existence of a film defect in step (c) by
        (i) selectively pulse polarizing said film face by small voltage cathodic-anodic pulses and computing the film face's film resistance from the polarizing pulses and detected induced pulse polarization current; said
        (ii) selectively subtracting a current correction portion, computed as caused by the film resistance, from said sweep polarization current to detect a comparatively very small current-potential variation and from this very small current-potential variation computing the specimen's corrosion current; and
    (f) responding to the computation of existence of a film defect in step (c) by detecting said sweep polarization current to selectively form cathodic polarization curves and anodic polarization curves.

2. The method of claim 1, wherein said method further comprises the step of computing, from said computed film resistance and induced pulse polarization current, the water merpeation rate of said film.

3. A method of testing coated metallic material for corrosion, comprising the steps of:
    (a) providing a metallic specimen plate having a film face coated by a film of paint and bringing the film face in contact with a corrosive test medium;
    (b) providing a non-film face, on the side of the plate reverse to said film face, and bringing the non-film face in contact with an alkaline solution;
    (c) potentiostatically electrolyzing said non-film face of said specimen plate, by a non-film face counter-electrode, at zero potential relative to the potential value of a non-film face reference electrode; and
    (d) detecting an electrolysis current flowing from said non-film face with the help of said second counter-electrode.

4. The method of claim 3, including a step of setting the temperature of said corrosive medium higher than the temperature of said alkaline solution to perform accelerated tests.

5. The method of claim 3, wherein step (c)'s cathodic-anodic voltage is in pulse form and when the detected induced polarization current has induced cathodic and anodic pulse of relatively substantially the same amplitude, said non-existence of a defect is computed.

6. A corrosion evaluation testing method of coated metallic material as claimed in claim 3, wherein when a peak exists in said negative polarization curve, said method further comprises the step of measuring selectively either or both of the potential and current values of said peak portion.

7. A corrosion evaluation testing method of coated metallic material as claimed in claim 6, wherein said method further comprises the step of measuring the time variation of said potential of said peak portion for each of said cathodic polarization curves which can be obtained for each given time of contact with said corrosive medium.

8. A corrosion evaluation testing method of coated metallic material as claimed in claim 6, wherein said mathod further comprises the step of measuring the time variation in said current of said peak portion for each of said cathodic polarization curves which can be obtained for each given time of contact with said corrosive medium.

9. A corrosion evaluation testing method of coated metallic material as claimed in claim 3, wherein said method further comprises the step of measuring the area relating to the peak portion, which is surrounded by two said polarization curves which can be obtained in an initial contacting stage between said corrosive medium and said specimen plate and can be obtained after a given time of contact, when said peak portion exists in said polarization curve.

10. A corrosion evaluation testing method of coated metallic material as claimed in claim 3, wherein said method further comprises the step of measuring the area relating to the peak portion, each of which is surrounded by said polarization curve and the Tafel slope specific to said polarization curve.

11. A corrosion evaluation testing method of coated metallic material as claimed in claim 10, wherein said method further comprises the step of obtaining said area of said peak portion for each immersing time and measuring the variation of said area with said immersing time.

12. A corrosion evaluation testing method of coated metallic material as claimed in claim 3, wherein said method further comprises the step of detecting the existence of a second peak in the time variation of said electrolysis current.

13. A corrosion evaluation testing method of coated metallic material as claimed in claim 3, wherein when the time variation of said electrolysis current has at least one peak, said method further comprises the step of detecting the quantity of electricity of each said peak.

14. A corrosion evaluation testing method of coated metallic material as claimed in claim 3, wherein said method further comprises the step of detecting either or both of the rising time and the rising slope of a third peak in the time variation of said electrolysis current.

15. A corrosion evaluation testing method of coated metallic material which comprises the steps of:
  applying DC voltage, at a constant potential sweep speed, between a coated specimen plate having defects and a counter electrode with a corrosive medium being interposed, thereby effecting cathodic polarization, after said coated specimen plate having defects has been potentiostatically electrolyzed at its spontaneous electrode potential and then detecting the variation in the potential relating to said coated specimen plate with the help of a reference electrode together with the variation in the current flowing between said coated specimen plate and said counter electrode;
  detecting the existence of a peak portion in the cathodic polarization curve formed from said variation in the potential and said variation in the current; and
  detecting whether said spontaneous electrode potential of said coated specimen plate is anodic or cathodic with respect to the spontaneous electrode potential of substrate metal obtained under substantially the same electrochemical conditions, whereby the corrosion form is judged.

16. A corrosion evaluation testing method of coated metallic material as claimed in claim 15, wherein said method further comprises the step of detecting the existence of a peak portion in the anodic polarization curve relating to said coated specimen plate.

17. A corrosion evaluation testing method of coated metallic material as claimed in claim 16, wherein said method further comprises the step of detecting the corrosion current from either or both of said cathodic polarization curve and said anodic polarization curve.

18. A corrosion evaluation testing method of coated metallic material as claimed in claim 17, wherein said method of further comprises the steps of:
  detecting the peak potential value, peak current value and the area relating said peak portion every for each immersing time; and
  measuring the variations of said peak potential value, said peak current value and said area with said immersing time.

19. A corrosion evaluation testing method of coated metallic material as claimed in claim 15, wherein said method further comprises the steps of:
  potentiostatically electrolyzing the non-film face side of said specimen plate at a potential necessary for hydrogen ionization of said non-film face side, with said film face side being under a corroding state, thereby to detect said electrolysis current; and
  selectively detecting the quantity of electricity relating to a second peak and following the time variation of said electrolysis current and the quantity of electricity relating to a third peak in said time variation of said electrolysis current, each of which corresponds to the amount of hydrogen dissolved in said substrate material due to corrosion on said film face side.

20. A corrosion evaluation testing apparatus which comprises:
  a pair of measuring cell vessels, which are so constructed that a coated metallic plate, at least one face of said plate being coated with film, is grasped by respective side edge portions of said paired measuring cell vessels at both its faces, a corrosive medium being filled in one of said paired measuring cell vessels on the film coated side of said coated metallic plate, a first reference electrode and a first counter electrode in said corrosive medium, the other one of said paired cell vessels, which is positioned on the uncoated side reverse to said film coated side, being filled with an alkaline solution, a second reference electrode and a second counter electrode being set in said alkaline solution;
  a first spontaneous electrode potential detecting means which is connected to said first reference electrode and said coated metallic plate, thereby to detect the electrode potential of the coated metallic plate in said corrosive medium;
  a first potentiostat means which is connected to said first counter electrode and said coated metallic plate thereby to potentiostatically electrolyze said coated metallic plate at its spontaneous electrode potential in response to a potential signal output from said first spontaneous electrode potential detecting means;
  a pulse potential applying means which is connected to said first counter electrode and said metallic plate thereby to apply cathodic-anodic pulsation potential between said first counter electrode and said coated metallic plate;
  a linear potential sweep applying means which is connected to said first counter electrode and said coated metallic plate thereby to apply sweep potential between said first counter electrode and said coated metallic plate, said sweep potential being arranged to be selectively varied in the anodic mode and in the cathodic mode;

a pulse polarization current detecting means for detecting anodic and cathodic pulsation polarization current flowing between said first counter electrode and said coated metallic plate through application of said cathodic-anodic pulsation potential;

a comparator means for comparing said anodic and cathodic pulsation polarization currents detected by said pulse polarization current detecting means;

a polarization current detecting means for detecting polarization current flowing between said first counter electrode and said coated metallic plate through application of said sweep potential;

a compensating means which is connected to said linear potential sweep applying means and said pulse polarization current detecting means thereby to subtract the polarization current portion specific to polarization effects caused by the electric resistance specific to said coated film from said anodic and cathodic pulsation polarization currents or from said polarization current caused by application of said sweep potential;

an infinitesimally small current detecting means capable for detecting infinitesimally small current compensated by said compensating means;

a second spontaneous electrode potential detecting means which is connected to said second reference electrode and said coated metallic plate thereby to detect the electrode potential of said coated metallic plate;

a second potentiostat means which is connected to said second counter electrode and said coated metallic plate thereby to set said coated metallic plate at relative zero potential with respect to said second reference electrode in response to a potentional signal output from said second spontaneous electrode potential detecting means;

an electrolysis current detecting means which is connected to said second counter electrode and said coated metallic plate thereby to detect the electrolysis current flowing between said second counter electrode and said coated metallic plate;

control means connected to each of the above-said means, thereby to control them for the measurement relating to said film coated side in the sequence set forth, said control means actuating said first spontaneous electrode potential detecting means and said first potentiostat means so that said coated metallic plate is potentiostatically electrolyzed at its spontaneous electrode potential, said control means actuating said pulse potential applying means, said pulse polarization current detecting means and said comparator means, said control means actuating said linear potential sweep applying means and said polarization current detecting means wherein when the signal output from said comparator means is a signal carrying non-defects information thereon, said compensating means and said infinitesimally small current detecting means are simultaneously actuated, whereby said measurement relating to said film coated side is conducted; prior to or subsequent to said measurement relating to said film coated side, said control means first actuating said second spontaneous electrode potential detecting means and said second potentiostat means thereby to set said coated metallic plate to relative zero potential with respect to said second reference electrode and thereafter to actuate said electrolysis current detecting means; and a collecting, recording and calculating means which is connected to at least said pulse potential applying means, said pulse polarization current detecting means, said linear potential sweep applying means, said polarization current detecting means, said infinitesimally small current detecting means and said electrolysis current detecting means thereby to operate selectively said anodic or cathodic polarization curve and said infinitesimally small current-potential variation curve, and if necessary to the time variation of said electrolysis current and to at least store said operating results.

21. A corrosion evaluation testing apparatus as claimed in claim 20, wherein said collecting, recording and calculating means calculates the electric resistance specific to said coated film in response to signals outputted from said pulse potential applying means and said pulse polarization current detecting means, said collecting, recording and calculating means being capable of calculating the water permeation rate from said electric resistance value of said coated film.

22. A corrosion evaluation testing apparatus as claimed in claim 20, wherein said collecting and recording and calculating means is adapted to calculate said corrosion current selectively from said cathodic and anodic polarization curves and from said infinitesimally small current-potential variation curve.

23. A corrosion evaluation testing apparatus as claimed in claim 20, wherein said apparatus further comprises a first peak detecting means for differentiating polarization current variation curve and a peak potential and/or current detecting means, respective input sides of both said means each being connected to said polarization current detecting means with respective output sides each being connected to said collecting, recording and calculating means, said output signal of said peak detecting means being selectively calculated and detected selectively by said collecting, recording and calculating means and a zero output detecting means to obtain a peak existence signal wherein the output of said peak potential and/or current detecting means is inputted to said collecting, recording and calculating means with the help of said control means in response to said peak existence signal and furthermore, with respect to said peak existence signal, the peak area relating to cathodic polarization curve which is selectively being formed and has been formed within said collecting, recording and calculating means is capable of being calculated and then stored in said collecting, recording and calculating means itself.

24. A corrosion evaluation testing apparatus as claimed in claim 20, wherein said apparatus further comprises an electrolysis current peak detecting means for differentiating electrolysis current variation, and electrolysis current peak area detecting means for integrating said electrolysis current variation and a time measuring means for measuring the time after the start of measurement, said electrolysis current detecting means being connected to respective input sides of said electrolysis current peak detecting means and said electrolysis current peak area detecting means with output side of said electrolysis current peak detecting means being connected selectively to said collecting, recording and calculating means and to said zero output detecting means selectively to calculate and to select said output signal of said electrolysis current peak detecting means thereby to actuate said time counting means to store and display the time variation of generation of said peak signal in response to a peak signal with the use of said control means as well as said electrolysis peak area detecting means so as to integrate said electrolysis current variation between said measuring start time and said time of generation of said peak signal and then to store and display the integral result.

25. A corrosion evaluation testing apparatus comprises:
  a peak detecting means for differentiating the cathodic polarization curve specific to a coated metallic material having film defects therein;
  a first spontaneous electrode potential detecting means for detecting the spontaneous electrode potential of said coated metallic material in the corrosive medium;
  a means for inputting the spontaneous electrode potential of the substrate metal of said coated metallic material under the same corrosive conditions as can be found in said corrosive medium;
  a calculating means whose input side is connected with said peak detecting means, said first spontaneous electrode potential detecting means and said inputting means, said calculating means being arranged to judge whether or not peak exists in said cathodic polarization curve in response to the signal outputted from said peak detecting means as well as whether said spontaneous electrode potential of said coated metallic material is relatively more anodic or more cathodic with respect to said spontaneous electrode potential of said substrate metal, thereby to detect either pitting or crevice corrosion through combination of said peak-existing signal or peak-absent signal and a resultant signal resultantly obtained from said comparison concerning the spontaneous electrode potential; and
  at least one displaying means.

26. A corrosion evaluation testing apparatus as claimed in claim 25, wherein said peak detecting means is adapted to differentiate the anodic polarization curve, said calculating means being further capable of adding said signal group selectively with a peak-existing signal in said anodic polarization curve and with a peak-absent signal in said anodic polarization curve, thereby to detect either said pitting corrosion or said crevice corrosion through the resultant combination of all said signals.

27. A corrosion evaluation testing apparatus as claimed in claim 26, wherein a cathodic and/or anodic polarization current inputting means used to obtain corrosion current and a means inputting said corrosion current are further connected to said input side of said calculating means, information relating to corrosion volume being obtained according to said input signal relating to said corrosion current being combined with the forming signal selectively concerned for said pitting or crevice corrosion to illustrate the corrosion in stereoscopic form with the use of said displaying means.

28. A corrosion evaluation testing apparatus as claimed in claim 27, wherein at least one of said means for inputting signals carrying a peak potential, peak current and/or peak areas each related to said cathodic polarization curve and a means for inputting the quantity of electricity specific to the second peak and following the electrolysis current variation is selectively connected to said input side of said calculating means, so that a signal outputted from said one of said two means can make it possible for said calculating means selectively to provide the rust width in the case of said crevice corrosion and to provide the depth of pitting in the case said pitting corrosion, whereby said displaying means is capable of illustrating said stereoscopic corrosion in a much detailed state.

* * * * *